(12) United States Patent
Sakamoto et al.

(10) Patent No.: US 7,674,533 B2
(45) Date of Patent: Mar. 9, 2010

(54) DIBENZOANTHRACENE DERIVATIVES, ORGANIC ELECTROLUMINESCENT DEVICES, AND DISPLAY APPARATUS

(75) Inventors: Yukinari Sakamoto, Tokyo (JP); Yoshihisa Miyabayashi, Kanagawa (JP); Tadahiko Yoshinaga, Kanagawa (JP)

(73) Assignee: Sony Corporation, Tokyo (JP)

( * ) Notice: Subject to any disclaimer, the term of this patent is extended or adjusted under 35 U.S.C. 154(b) by 513 days.

(21) Appl. No.: 11/583,645

(22) Filed: Oct. 17, 2006

(65) Prior Publication Data

US 2007/0087223 A1 Apr. 19, 2007

(30) Foreign Application Priority Data

Oct. 19, 2005 (JP) ............................. P2005-304047

(51) Int. Cl.
*H01L 51/54* (2006.01)
*C09K 11/06* (2006.01)
*C07C 211/61* (2006.01)

(52) U.S. Cl. .................. 428/690; 428/917; 313/504; 313/506; 564/426; 564/434; 257/E51.049; 257/E51.051

(58) Field of Classification Search ...................... None
See application file for complete search history.

(56) References Cited

U.S. PATENT DOCUMENTS

2003/0091860 A1* 5/2003 Oshiyama et al. ............ 428/690

FOREIGN PATENT DOCUMENTS

JP 09-268283 10/1997

(Continued)

OTHER PUBLICATIONS

JPO Machine translation for JP 2006-151844 A, publication date Jun. 2006.*

*Primary Examiner*—Dawn Garrett
(74) *Attorney, Agent, or Firm*—Robert J. Depke; Rockey, Depke & Lyons, LLC

(57) ABSTRACT

Dibenzoanthracene derivatives are each substituted by an amino compound group at least one of 9-position and 14-position of a dibenzo[a,c]anthracene skeleton and represented by the following formula (1) or (2):

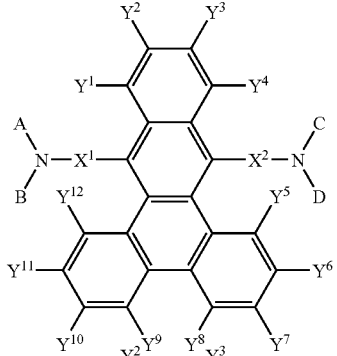

Formula (1)

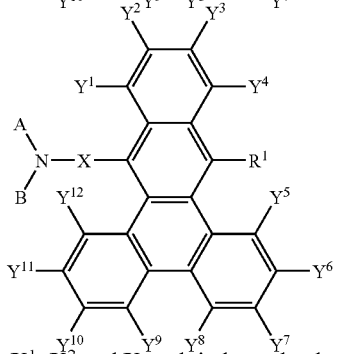

Formula (2)

wherein $X^1$, $X^2$ and $X$ each independently represents a substituted or unsubstituted arylene or divalent heterocyclic group; A, B, C and D each independently represents a substituted or unsubstituted alkyl, aryl heterocyclic group, and between the adjacent groups, may be fused together to form rings; and $Y^1$ to $Y^{12}$ and $R^1$ each independently represents a hydrogen atom, a halogen atom, an alkoxy group, or a substituted or unsubstituted alkyl, aryl or heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings.

13 Claims, 2 Drawing Sheets

FOREIGN PATENT DOCUMENTS

| | | |
|---|---|---|
| JP | 09-268284 | 10/1997 |
| JP | 2001-284050 | 10/2001 |
| JP | 2003-146951 | 5/2003 |
| JP | 2004-067528 | 3/2004 |
| JP | 2006-151844 A * | 6/2006 |

* cited by examiner

DIBENZOANTHRACENE DERIVATIVES, ORGANIC ELECTROLUMINESCENT DEVICES, AND DISPLAY APPARATUS

CROSS REFERENCES TO RELATED APPLICATIONS

The present invention contains subject matter related to Japanese Patent Application JP 2005-304047, filed in the Japanese Patent Office on Oct. 19, 2005, the entire contents of which being incorporated herein by reference.

BACKGROUND OF THE INVENTION

1. Field of the Invention

This invention relates to dibenzoanthracene derivatives suitably usable as organic materials for organic electroluminescent devices, electroluminescent devices making use of the electroluminescent derivatives, and display apparatus making use of the electroluminescent devices.

2. Description of the Related Art

As self-emitting flat panel displays of low power consumption, high response speed and no viewing angle dependency, display apparatus making use of organic electroluminescent devices (so-called organic EL devices) have been drawing attention in recent years.

An organic electroluminescent device is provided between an anode and a cathode with an organic layer, which contains an organic light-emitting material capable of emitting light when a current is fed. Developed as such organic layers include, for example, a construction that a hole transport layer, a light-emitting layer with an organic light-emitting material contained therein, and an electron transport layer are stacked one over another from the side of the anode, and a construction that a light-emitting material is included in an electron transport layer to form an electron-transporting, light-emitting layer.

Organic electroluminescent devices of such a construction are self-emitting devices. When constructing a display apparatus by using these organic electroluminescent devices, it is, therefore, most important requirements to provide them with a longer service life and to ensure their reliability. Accordingly, research is now under way on organic materials that make up organic electroluminescent devices.

Concerning materials equipped with the anthracene skeleton among such organic materials, numerous derivatives have been investigated such as anthracene derivatives and bisanthracene derivatives having one or more amino or aryl groups and anthracene derivatives having one or more styryl groups. For example, refer to Japanese Patent Laid-open Nos. 2003-146951 (Patent Document 1), Hei 09-268284 (Patent Document 2), Hei 09-268283 (Patent Document 3), 2004-67528 (Patent Document 4), and 2001-284050 (Patent Document 5) for more information.

For example, Patent Document 1 discloses the use of 2,6-disubstituted 9,10-diarylanthracene compounds, each of which contains aryl groups substituted to the 9- and 10-positions of anthracene and also particular substituent groups introduced to the 2- and 6-positions of anthracene, as materials for forming hole transport layers. Among the materials for forming hole transport layers, aromatic amine compounds equipped with fluorescence are described to be usable as materials for light-emitting layers. Patent Document 2, on the other hand, discloses that compounds containing arylamino groups substituted to the 9- and 10-positions of anthracene can be effectively used as light-transmitting materials.

In the meantime, a variety of investigations have also been made on organic light-emitting materials capable of emitting blue, green and red colors, respectively, with a view to realizing a full color display on a display apparatus that makes use of organic electroluminescent devices. Regarding blue-light emitting materials, in particular, further improvements are required in color purity, luminescence efficiency and light-emitting life. Accordingly, improvements are now underway, for example, with respect to stilbene, styrylallene and anthracene derivatives. For more information, refer to Non-patent Document 1 (Materials Science and Engineering: R: Reports, 39(5-6), 143-222 (2002)) and Non-patent Document 2 (Applied Physics Letters (USA), 67(26), 3853-3855 (1995)), for example.

SUMMARY OF THE INVENITON

However, no blue-light emitting material of high color purity has been found yet to be practically satisfactory in both luminescence efficiency and light-emitting life.

Described specifically, it is difficult to achieve sufficiently high luminescence efficiency and light-emitting life even when organic electroluminescent devices are formed using the blue-light emitting materials disclosed in Non-patent Document 1 or 2. Even when organic electroluminescent devices are formed using the arylaminoanthracene derivatives disclosed in Patent Document 2, their luminescent colors range from a green color to a yellow color, and luminescence in a blue color range is hardly available.

Therefore, it is desirable to provide a dibenzoanthracene derivative suited for use as a blue-light emitting material in organic electroluminescent devices and capable of forming organic electroluminescent devices high in luminescence efficiency and excellent in light-emitting life and to provide organic electroluminescent devices making use of the dibenzoanthracene derivative and a display apparatus making use of the organic electroluminescent devices.

To satisfy these desires, the present invention provides in one embodiment thereof a dibenzoanthracene derivative substituted by an amino compound group at least one of 9-position and 14-position of a dibenzo[a,c]anthracene skeleton and represented by the following formula (1) or (2):

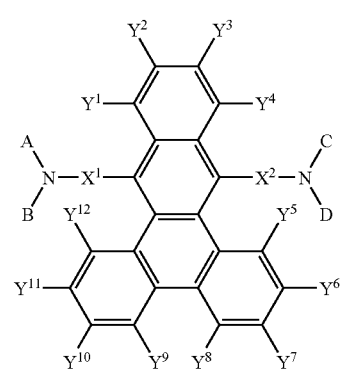

Formula (1)

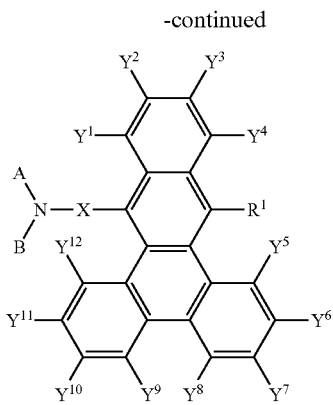

Formula (2)

In the formulas, $X^1$, $X^2$ and X each independently represents a substituted or unsubstituted arylene group or a substituted or unsubstituted divalent heterocyclic group. A, B, C and D each independently represents a substituted or unsubstituted alkyl group, a substituted or unsubstituted aryl group or a substituted or unsubstituted heterocyclic group, and between the adjacent groups, may be fused together to form rings. $Y^1$ to $Y^{12}$ and $R^1$ each independently represents a hydrogen atom, a halogen atom, a substituted or unsubstituted alkyl group, an alkoxy group, a substituted or unsubstituted aryl group, or a substituted or unsubstituted heterocyclic group. When $Y^1$ to $Y^{12}$ and $R^1$ are other than a hydrogen atom or a halogen atom, $Y^1$ to $Y^{12}$ and $R^1$ may be fused together between the adjacent groups to form rings.

It is to be noted that the term "alkyl group" referred to in the above encompasses therein "a linear alkyl group", "a branched alkyl group" and "a cyclic alkyl group".

The present invention provides in another embodiment thereof an organic electroluminescent device making use of the dibenzoanthracene derivative represented by the formula (1) or (2). This organic electroluminescent device is provided with an organic layer, which has at least a light-emitting layer and is held between a pair of electrodes. The above-mentioned dibenzoanthracene derivative is used in the organic layer. In particular, this dibenzoanthracene is preferably usable as a material that forms the light-emitting layer.

The dibenzoanthracene derivative represented by the formula (1) or (2) as described above can be suitably used as a light-emitting material or hole transport material for organic electroluminescent devices as will be described specifically in embodiments to be described subsequently herein. Organic electroluminescent devices making use of such dibenzoanthracene derivatives as light-emitting materials have been confirmed to provide a blue emission of high color purity at high brightness. It has also been confirmed that the brightness decrement is low in organic electroluminescent devices having organic layers formed with such dibenzoanthracene derivatives.

The present invention also provides in a further embodiment thereof a display apparatus making use of at least one organic electroluminescent device of the above-described construction. Especially preferably, organic electroluminescent devices of the above-described construction are arranged as blue-color emitting devices at some of plural pixels.

In such a display apparatus, the display apparatus is constructed using, as blue-color emitting devices, organic electroluminescent devices high in color purity and brightness and low in brightness decrement as mentioned above. A combination with other red-color emitting devices and green-color emitting devices makes it possible to perform a full-color display of high color reproducibility.

As has been described above, the construction of an organic electroluminescent device with the dibenzoanthracene derivative of one embodiment of the present invention as represented by the formula (1) or (2) can realize a blue emission, which is high in luminescence efficiency, low in decrement, excellent in life characteristics, and high in color purity.

According to the display apparatus of one embodiment of the present invention, the display apparatus can be constructed using, as blue-light emitting devices, the organic electroluminescent devices which are high in luminescence efficiency and excellent in life characteristics and permit a blue emission as mentioned above. A combination with other red-color emitting devices and green-color emitting devices, therefore, makes it possible to perform a full-color display of high color reproducibility and reliability.

DETAILED DESCRIPTION OF THE PREFERRED EMBODIMENTS

Figure 1:
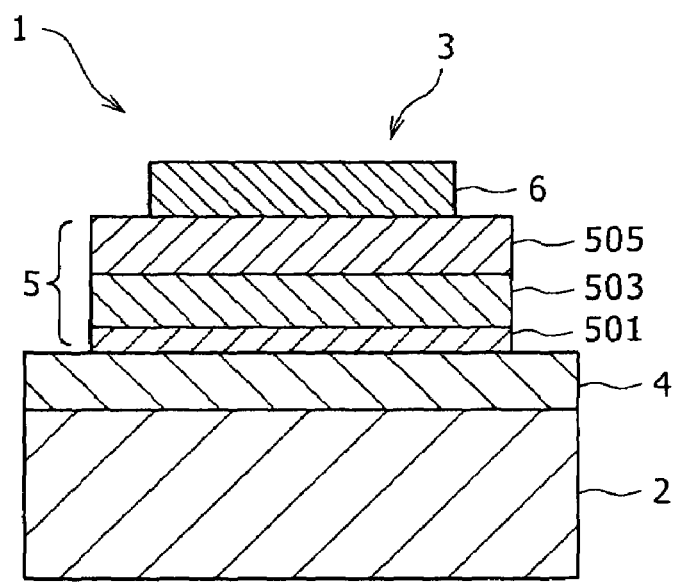
FIG. 1 is a cross-sectional view illustrating the construction of an organic electroluminescent device according to the present invention.

Embodiments of the present invention will hereinafter be described.

<Dibenzoanthracene Derivative>

More specific examples of the dibenzoanthracene derivative according to the present invention will next be described. The dibenzoanthracene derivative according to one embodiment of the present invention carries an amino compound group at least one of the 9- and 14-positions of the dibenzo[a,c]anthracene skeleton as represented by the following formula (1) or (2):

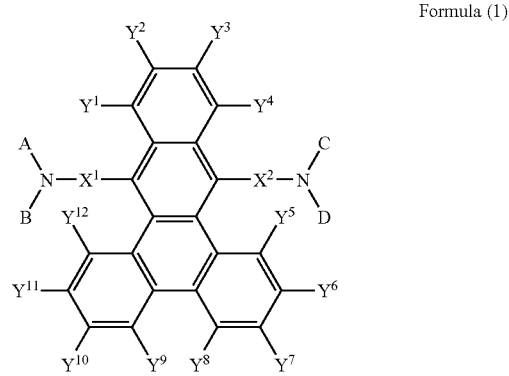

Formula (1)

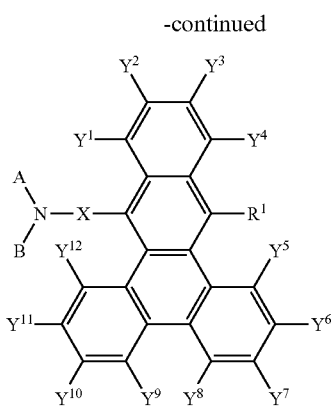

Formula (2)

$X^1$, $X^2$ and X in the above formula (1) or (2) each independently represents:
(a) a substituted or unsubstituted C6-28 arylene group, or
(b) a substituted or unsubstituted divalent C5-21 heterocyclic group.

Examples of the arylene group (a) include phenylene and divalent groups derived from the following aromatic hydrocarbons: biphenyl, terphenyl, naphthalene, anthracene, phenanthrene, pyrene, fluorene, fluoranthene, benzofluoranthene, dibenzofluoranthene, acephenanthrylene, aceanthrylene, triphenylene, acenaphthotriphenylene, chrysene, perylene, benzochrysene, naphthacene, plaiadene, picene, pentaphene, pentacene, tetraphenylene, trinaphthylene, benzophenanthrene, dibenzonaphthacene, benzoanthracene, dibenzoanthracene, benzonaphthacene, naphthopyrene, benzopyrene, dibenzopyrene, benzocyclooctene, anthranaphthacene, acenaphthofluorane, etc. Further, the arylene group (a) can also be a divalent group derived from a combination of two or more of these aromatic hydrocarbons.

It is to be noted that no particular limitation is imposed on the position(s) of substitution on the arylene group (a). For obtaining a blue emission of higher color purity, a preferred bonding configuration can be that the number of carbon atoms in each aromatic hydrocarbon bonded directly to the corresponding nitrogen atom is from 6 to 18, and a more preferred bonding configuration can be that the number of carbon atoms in each aromatic hydrocarbon bonded directly to the corresponding nitrogen atom is from 6 to 14.

On the other hand, examples of the divalent heterocyclic group (b) include divalent groups derived from thiophene, benzothiophene, oxazole, benzoxazole, oxadiazole, pyridine, pyrimidine, pyrazine, quinoline, benzoquinoline, dibenzoquinoline, isoquinoline, benzoisoquinoline, quinazoline, quinoxaline, acridine, phenanthridine, phenazine, and phenoxazine; and divalent groups derived from combinations thereof.

It is to be noted that no particular limitation is imposed on the position(s) of substitution on the divalent heterocyclic group (b). For obtaining a blue emission of higher color purity, a preferred bonding configuration can be that the number of carbon atoms in each heterocyclic group bonded directly to the corresponding nitrogen atom is from 5 to 17, and a more preferred bonding configuration can be that the number of carbon atoms in each heterocyclic group bonded directly to the corresponding nitrogen atom is from 5 to 13.

Further, $X^1$, $X^2$ and X in the formulas (1) and (2) may each independently be a divalent group formed by bonding the above-exemplified arylene group (a) and heterocyclic group (b) together.

As substituent atoms and/or groups to the arylene group (a) and the divalent heterocyclic group (b), illustrative are halogen atoms, hydroxyl group, substituted or unsubstituted amino compound groups, substituted or unsubstituted alkyl groups, substituted or unsubstituted alkenyl groups, substituted or unsubstituted cycloalkyl groups, substituted or unsubstituted alkoxy groups, substituted or unsubstituted aromatic hydrocarbon groups, substituted or unsubstituted aromatic heterocyclic groups, substituted or unsubstituted aralkyl groups, substituted or unsubstituted aryloxy groups, substituted or unsubstituted alkoxycarbonyl groups, and carboxyl group. No particular limitations are imposed on the number of substituent atom(s) and/or group(s) and the position(s) of substitution on the fused ring. Examples of the halogen atoms include fluorine, chlorine, bromine and iodine.

Next, A, B, C and D in the formulas (1) and (2) each independently represents:
(c) a substituted or unsubstituted C1-20 alkyl group,
(d) a substituted or unsubstituted C6-28 aryl group, or
(e) a substituted or unsubstituted C5-21 heterocyclic group.

Of these, the alkyl group (c) can be in any one of linear, branched and cyclic forms. Illustrative are methyl, ethyl, propyl, isopropyl, n-butyl, s-butyl, isobutyl, t-butyl, n-pentyl, n-hexyl, n-heptyl, n-octyl, hydroxymethyl, 1- hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, and 4-methylcyclohexyl.

Examples of the aryl group (d) include phenyl and monovalent groups derived from the following aromatic hydrocarbons: biphenyl, terphenyl, naphthalene, anthracene, phenanthrene, pyrene, fluorene, fluoranthene, benzofluoranthene, dibenzofluoranthene, acephenanthrylene, aceanthrylene, triphenylene, acenaphthotriphenylene, chrysene, perylene, benzochrysene, naphthacene, plaiadene, picene, pentaphene, pentacene, tetraphenylene, trinaphthylene, benzophenanthrene, dibenzonaphthacene, benzoanthracene, dibenzoanthracene, benzonaphthacene, naphthopyrene, benzopyrene, dibenzopyrene, benzocyclooctene, anthranaphthacene, acenaphthofluorane, etc. Further, the aryl group (d) can also be a monovalent group derived from a combination of two or more of these aromatic hydrocarbons.

It is to be noted that no particular limitation is imposed on the position(s) of substitution on the aryl group (d). For obtaining a blue emission of high color purity, a preferred bonding configuration can be that the number of carbon atoms in each aromatic hydrocarbon bonded directly to the corresponding nitrogen atom is from 6 to 18, and a more preferred bonding configuration can be that the number of carbon atoms in each aromatic hydrocarbon bonded directly to the corresponding nitrogen atom is from 6 to 14.

On the other hand, examples of the heterocyclic group (e) include monovalent groups derived from thiophene, benzothiophene, oxazole, benzoxazole, oxadiazole, pyridine, pyrimidine, pyrazine, quinoline, benzoquinoline, dibenzoquinoline, isoquinoline, benzoisoquinoline, quinazoline, quinoxaline, acridine, phenanthridine, phenazine, and phenoxazine; and monovalent groups derived from combinations thereof.

It is to be noted that no particular limitation is imposed on the position(s) of substitution on the heterocyclic group (e). For obtaining a blue emission of high color purity, a preferred bonding configuration can be that the number of carbon atoms in each heterocyclic group bonded directly to the corresponding nitrogen atom is from 5 to 17, and a more preferred bonding configuration can be that the number of carbon atoms in each heterocyclic group bonded directly to the corresponding nitrogen atom is from 5 to 13.

Further, A, B, C and D in the formulas (1) and (2) may each independently be a monovalent group formed by bonding the above-exemplified arylene group (e) and heterocyclic group (e) together.

As substituent atoms and/or groups to the aryl group (d) and the heterocyclic group (e), illustrative are halogen atoms, hydroxyl group, substituted or unsubstituted amino compound groups, substituted or unsubstituted alkyl groups, substituted or unsubstituted alkenyl groups, substituted or unsubstituted cycloalkyl groups, substituted or unsubstituted alkoxy groups, substituted or unsubstituted aromatic hydrocarbon groups, substituted or unsubstituted aromatic heterocyclic groups, substituted or unsubstituted aralkyl groups, substituted or unsubstituted aryloxy groups, substituted or unsubstituted alkoxycarbonyl groups, and carboxyl group. No particular limitations are imposed on the number of substituent atom(s) and/or group(s) and the position(s) of substitution on the fused ring. Examples of the halogen atoms include fluorine, chlorine, bromine and iodine.

It is to be noted that the introduction of appropriately bulky substituent groups as A, B, C and D in the formulas (1) and (2) is effective for the control of crystallization and for the suppression of bimolecular excitation, the crystallization and bimolecular excitation being relevant to device characteristics, and makes it possible to make further improvements in luminescence efficiency and light-emitting life. Suitably usable as these A, B, C and D can be those formed by introducing into the aryl group (d) or heterocyclic group (e) a substituent group selected from an alkyl, alkoxy, alkenyl or heterocyclic group.

Compounds of the formula (1) or (2), in which A and B or C and D are linked together via a single bond or a carbocyclic bond, are equipped with improved glass transition temperatures, respectively, so that they are excellent in heat resistance.

In the formulas (1) and (2), $Y^1$ to $Y^{12}$ and $R^1$ each independently represents:
(f) a hydrogen or halogen atom,
(g) a substituted or unsubstituted C1-20 alkyl group,
(h) a C1-20 alkoxy group,
(i) a substituted or unsubstituted C6-28 aryl group, or
(j) a substituted or unsubstituted C5-21 heterocyclic group.

In the case of a hydrogen or halogen atom (f), examples of the halogen atom include fluorine, chlorine, bromine and iodine.

The alkyl group (g) is similar to the alkyl group (c) described above in connection with A and B.

The alkoxy group (h) is represented by —OR, and as R, illustrative are methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl.

The aryl group (i) is similar to the aryl group (d) described above in connection with A, B, C and D.

The heterocyclic group (j) is similar to the heterocyclic group (e) described above in connection with A, B, C and D.

As specific examples of a dibenzoanthracene derivative that carries amino compound groups at both the 9- and 14-positions of a dibenzo[a,c]anthracene skeleton as represented by the formula (1), the following compounds (1)-d to compounds (46)-d will be shown although the present invention shall not be limited to them.

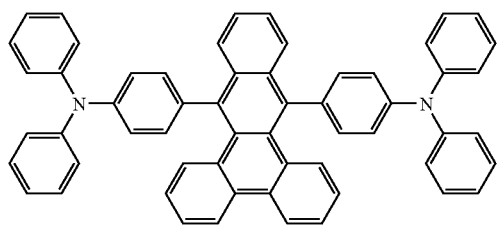

Compound (1)-d

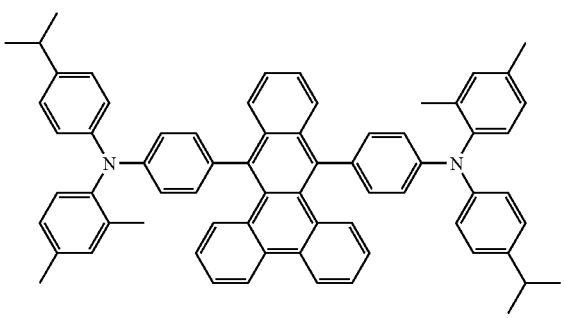

Compound (2)-d

-continued
Compound (3)-d
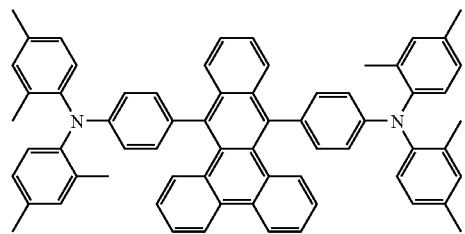
Compound (4)-d
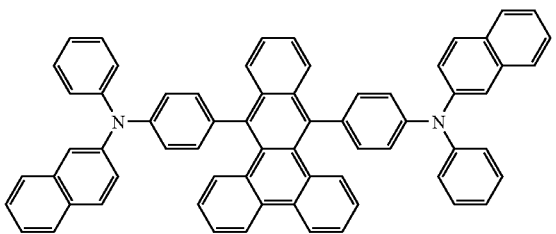
Compound (5)-d
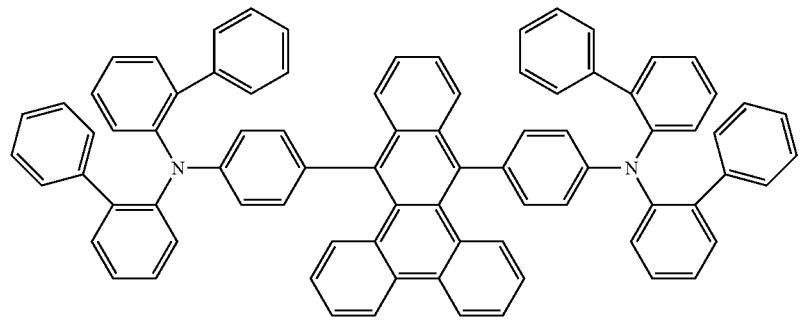
Compound (6)-d
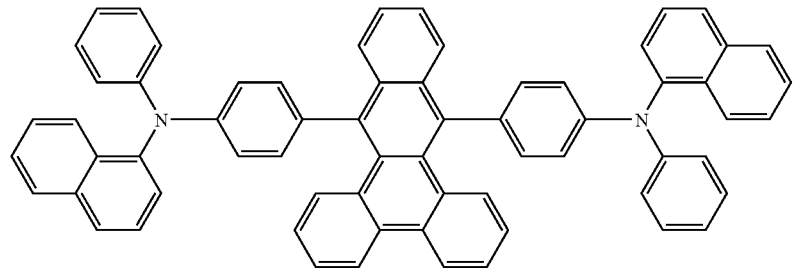
Compound (7)-d
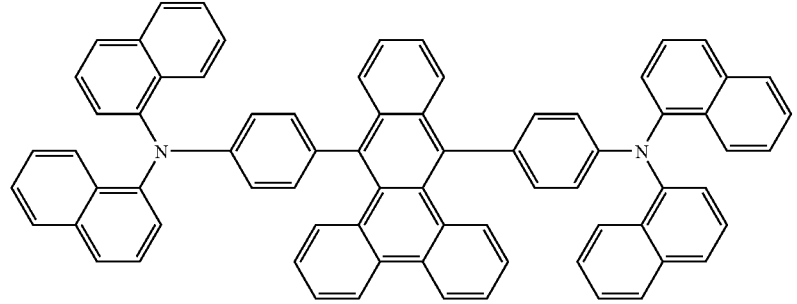
Compound (8)-d
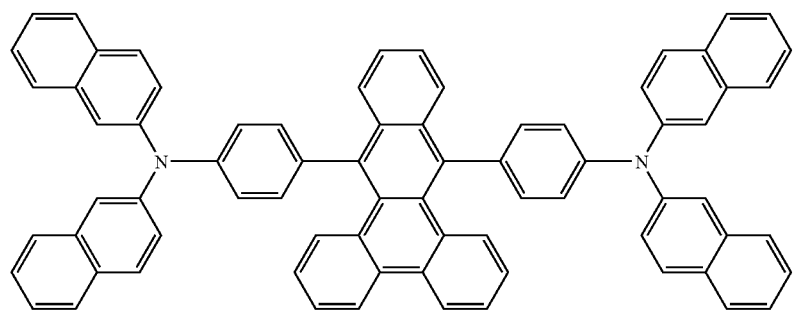

-continued
Compound (9)-d
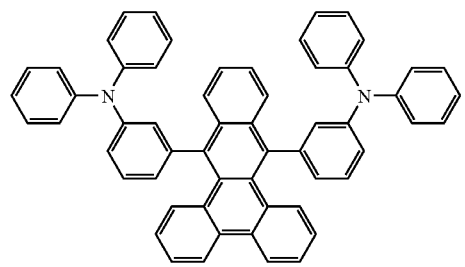
Compound (10)-d
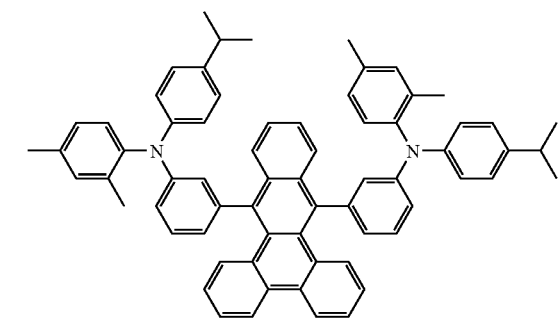
Compound (11)-d
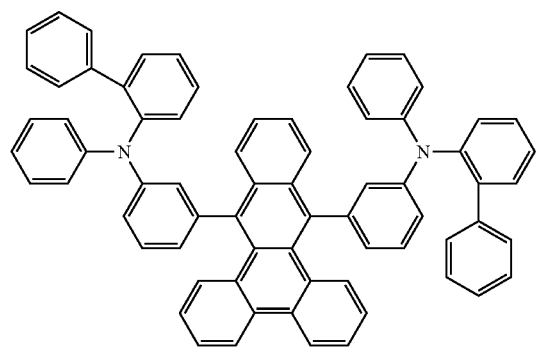
Compound (12)-d
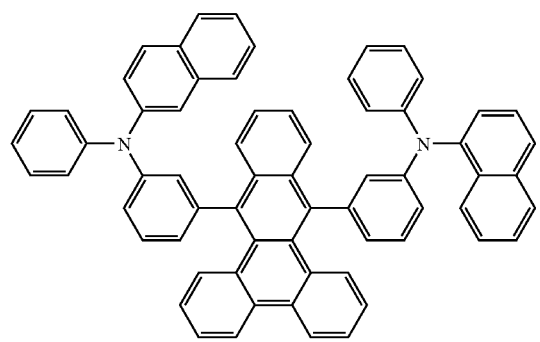
Compound (13)-d
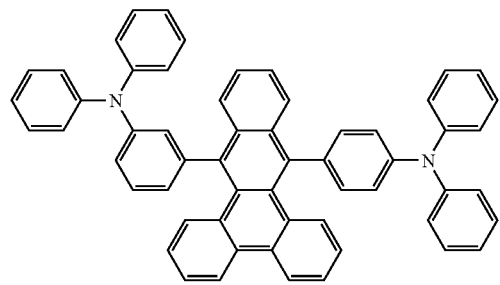
Compound (14)-d
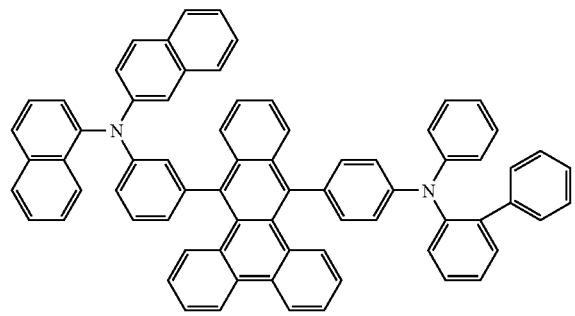
Compound (15)-d
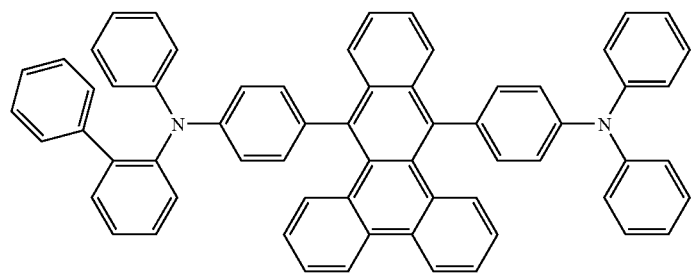
Compound (16)-d
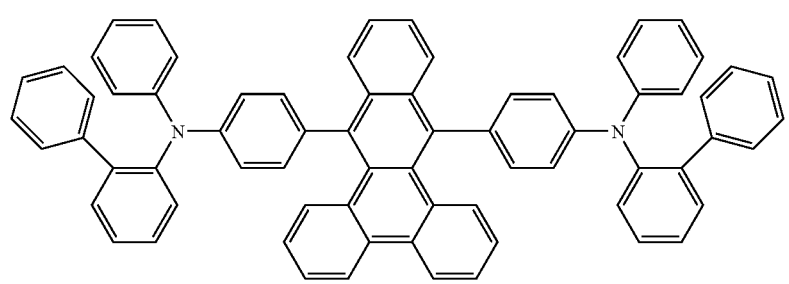

-continued
Compound (17)-d
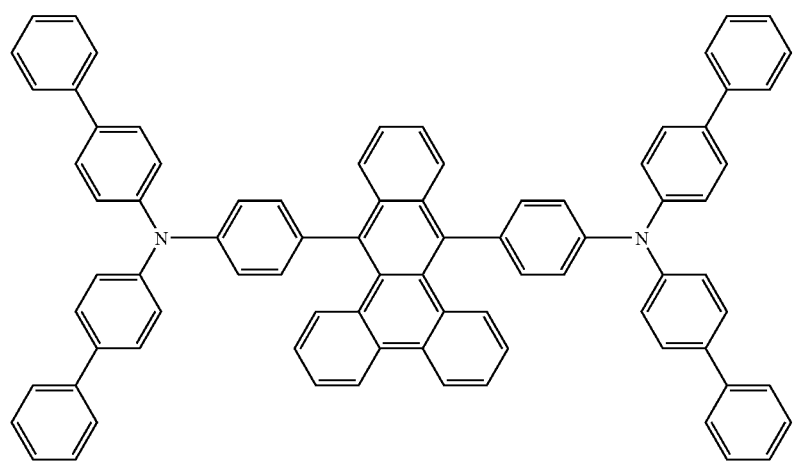
Compound (18)-d
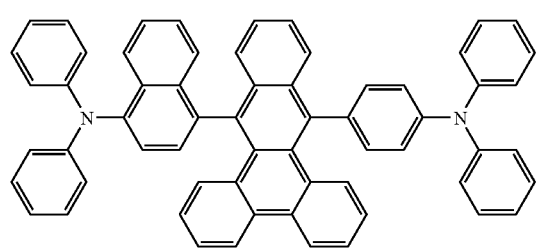
Compound (19)-d
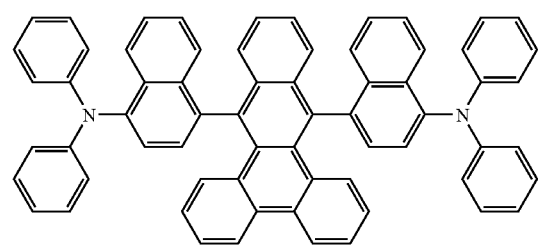
Compound (20)-d
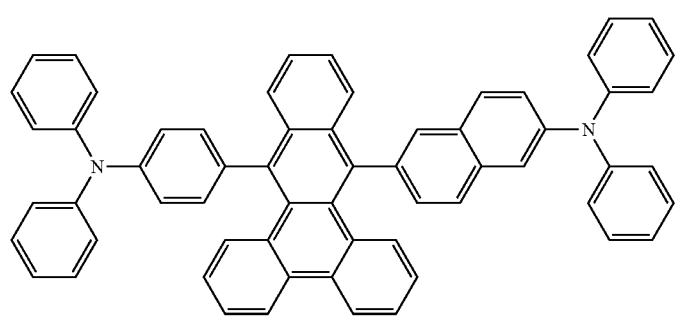
Compound (21)-d
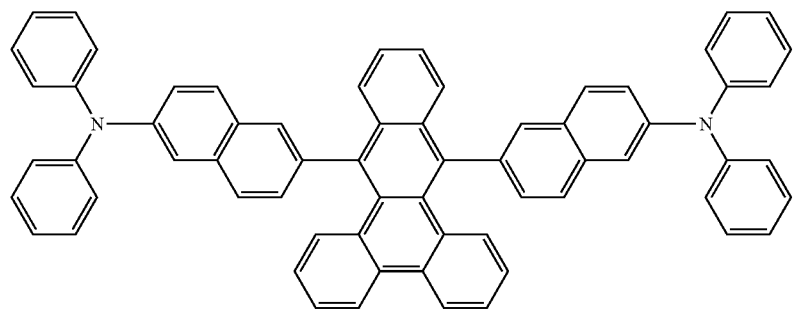

-continued
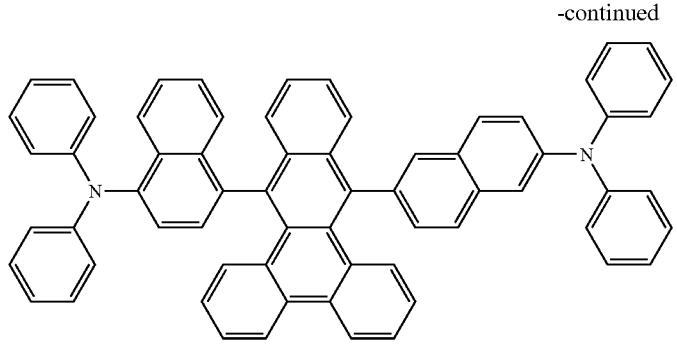
Compound (22)-d
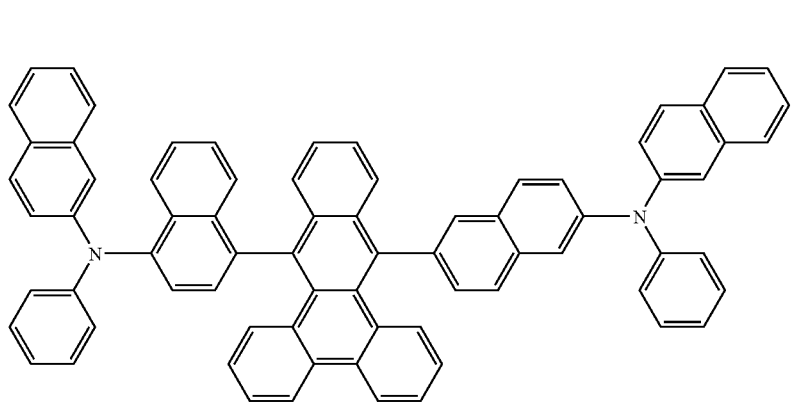
Compound (23)-d
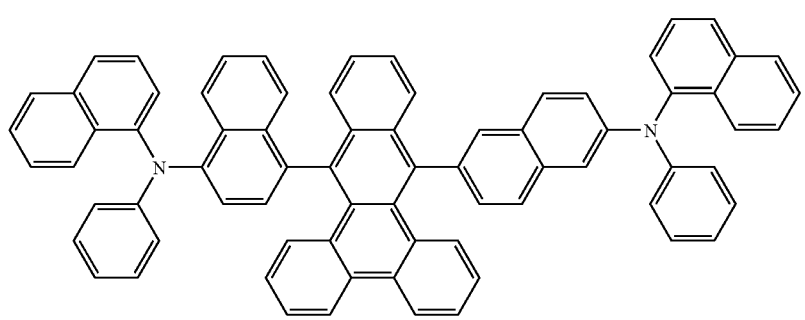
Compound (24)-d
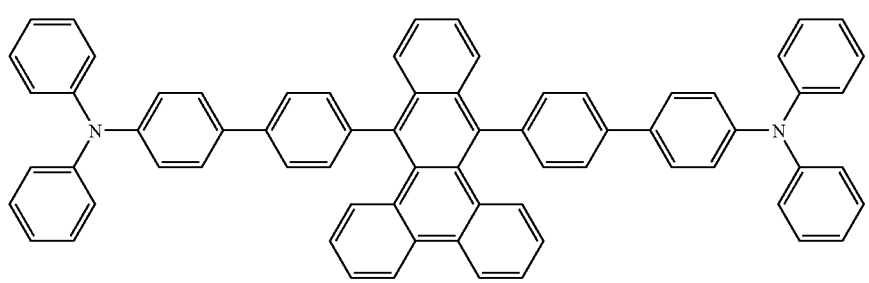
Compound (25)-d
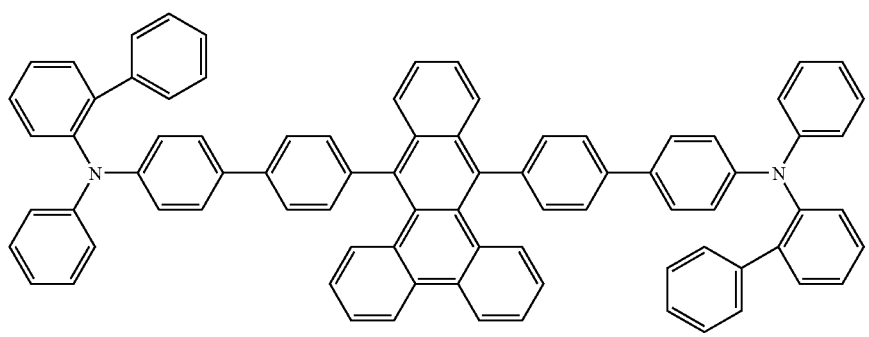
Compound (26)-d -continued
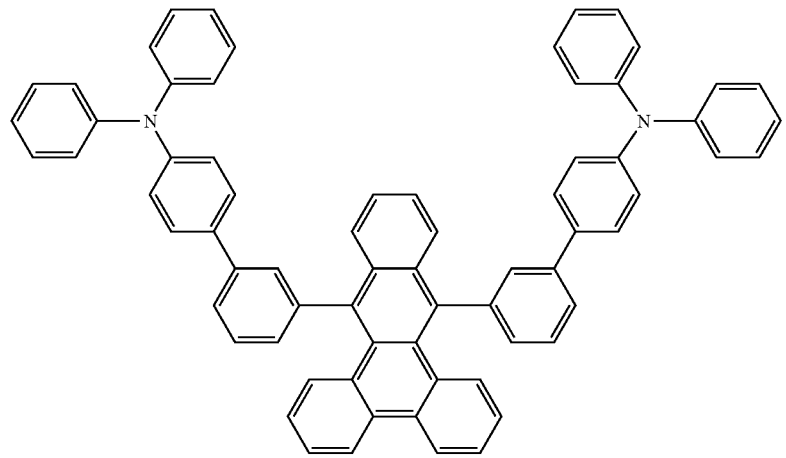
Compound (27)-d
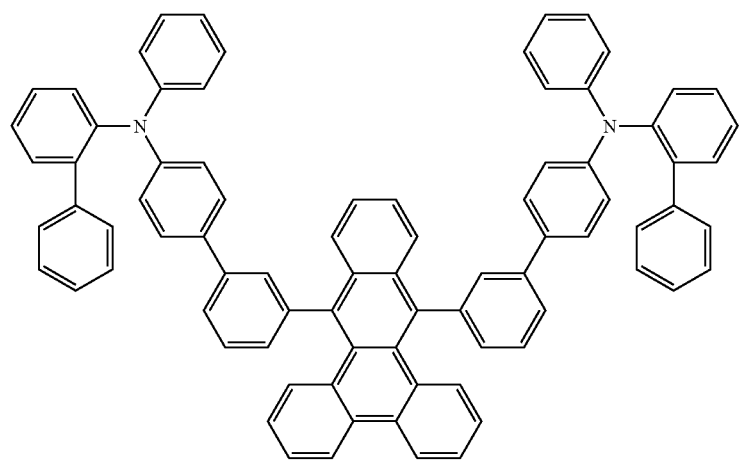
Compound (28)-d
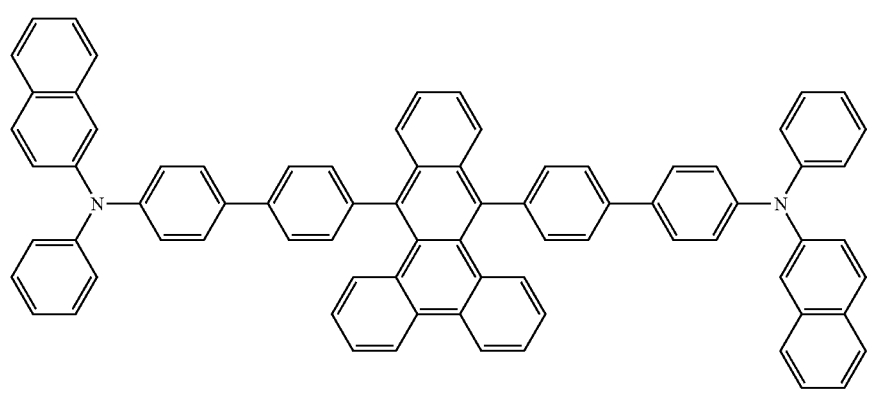
Compound (29)-d
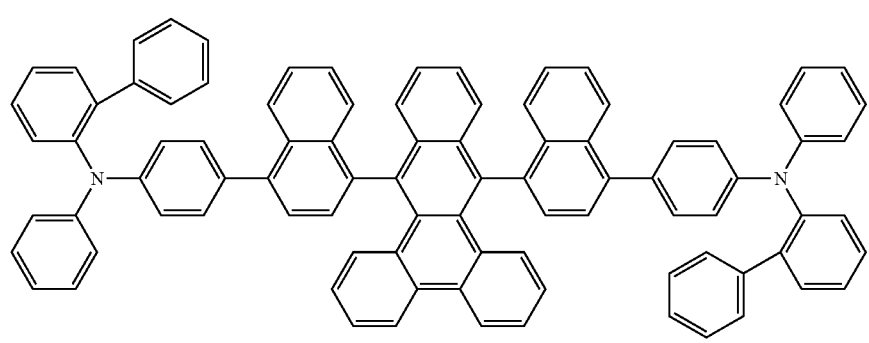
Compound (30)-d -continued
Compound (31)-d
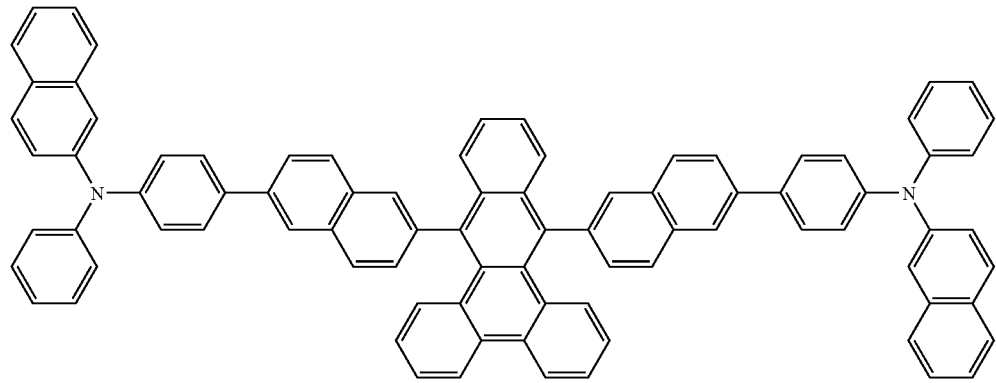
Compound (32)-d
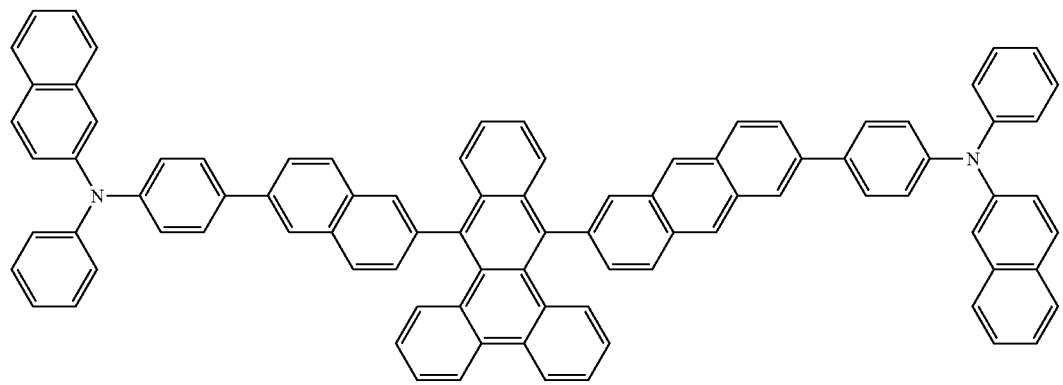
Compound (33)-d
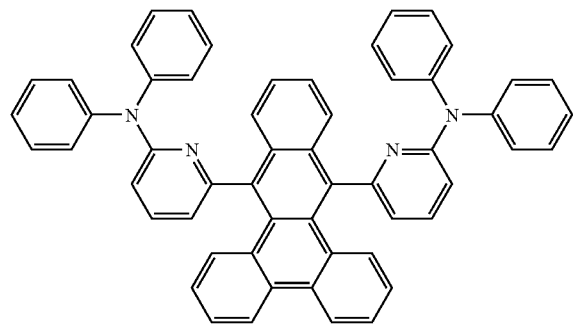
Compound (34)-d
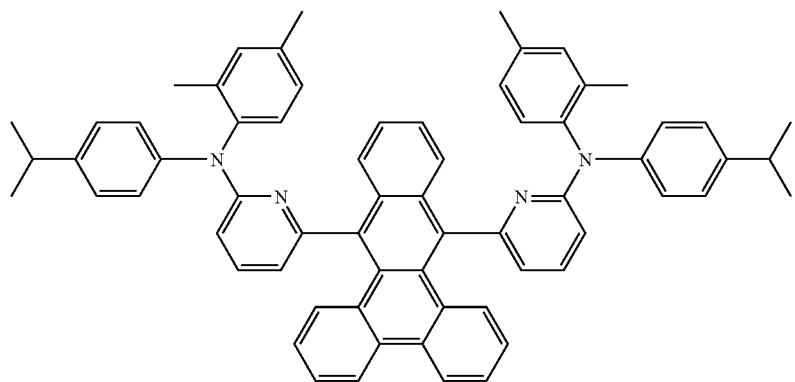

-continued
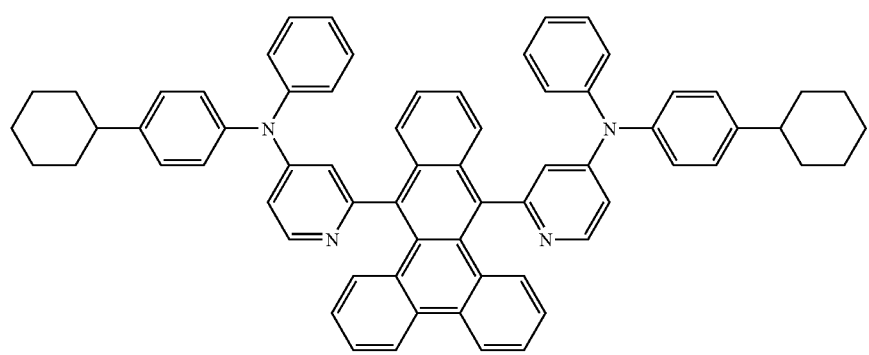
Compound (35)-d
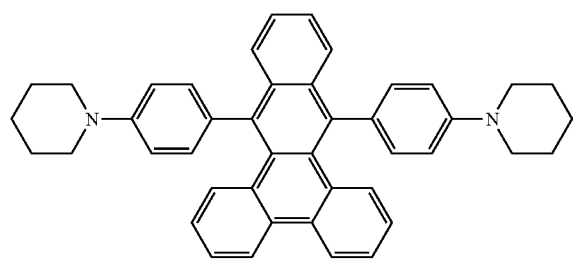
Compound (36)-d
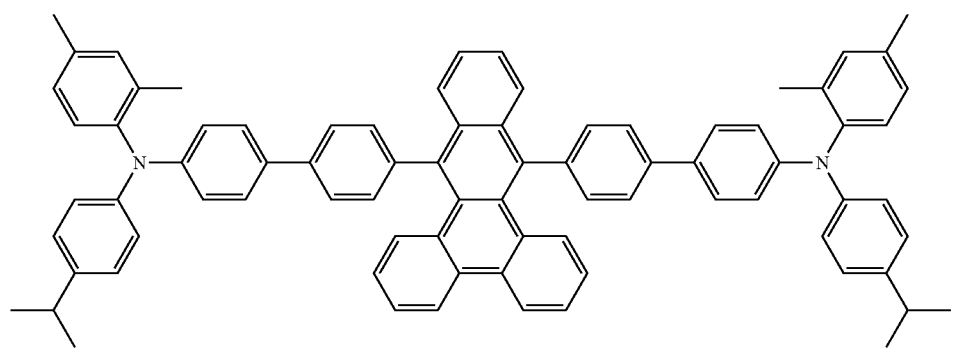
Compound (37)-d
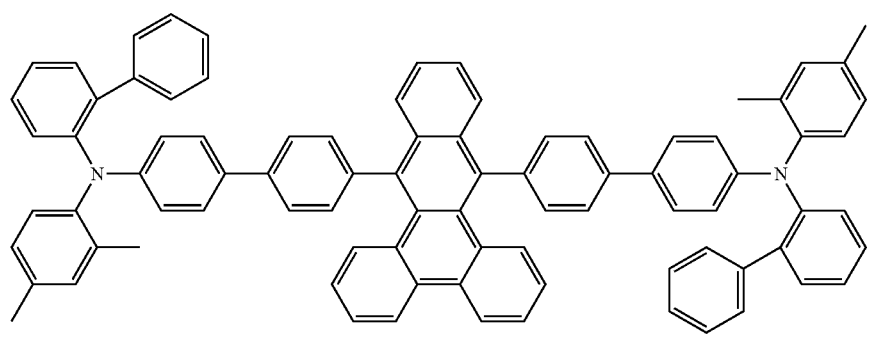
Compound (38)-d -continued
Compound (39)-d
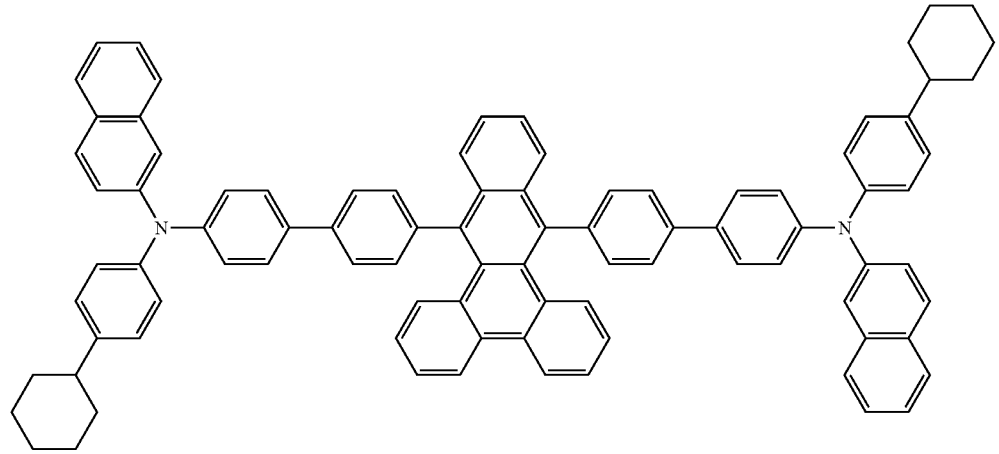
Compound (40)-d
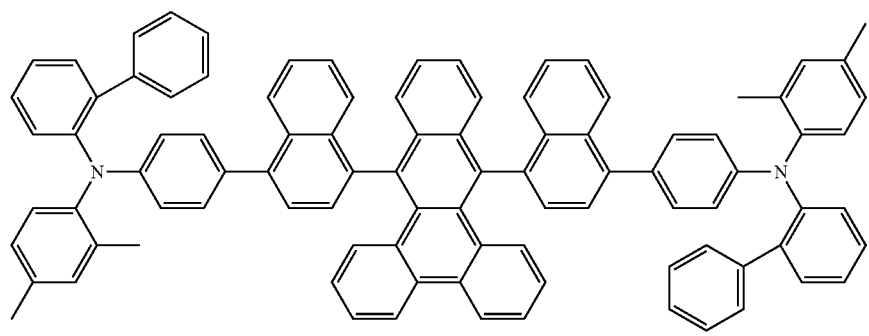
Compound (41)-d
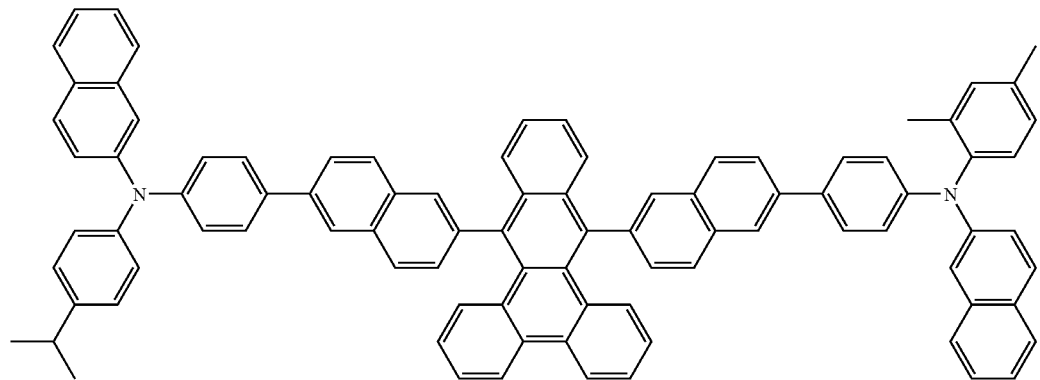
Compound (42)-d
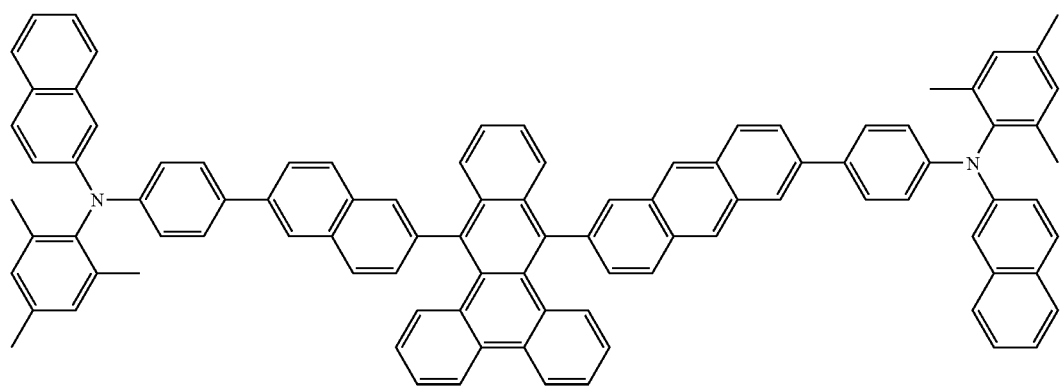

-continued
Compound (43)-d
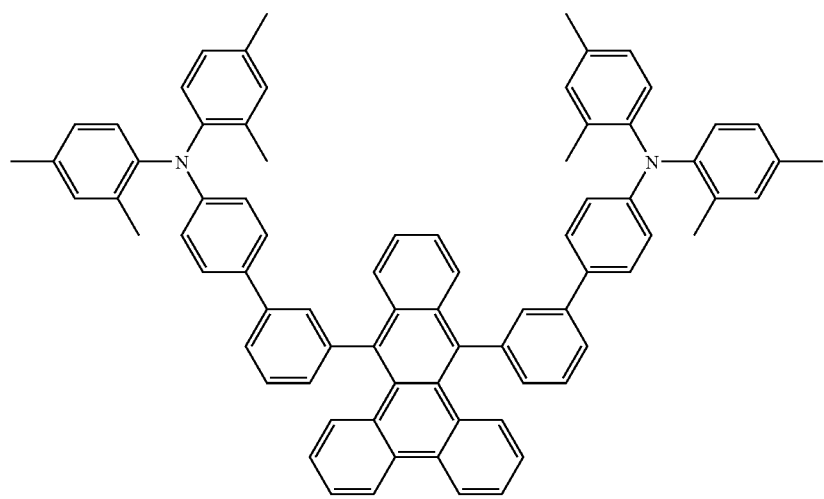
Compound (44)-d
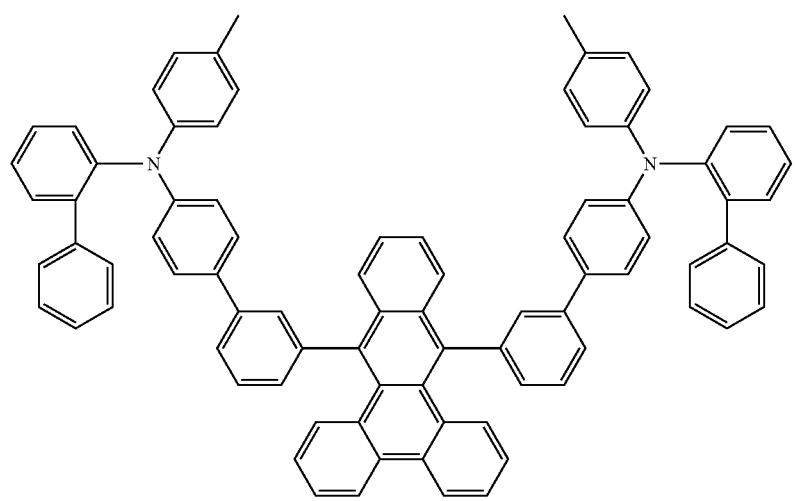
Compound (45)-d
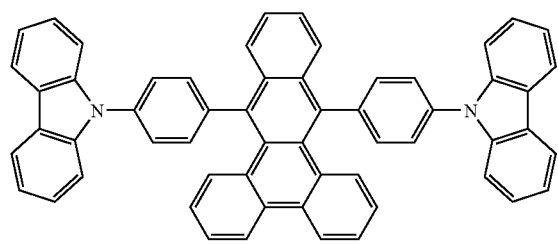
Compound (46)-d
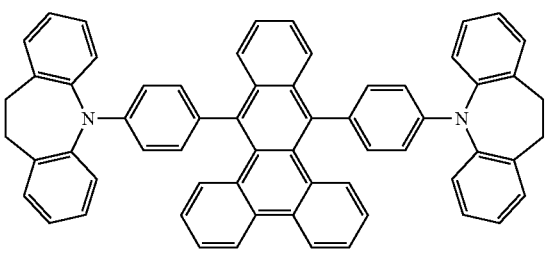

Next, as specific examples of a dibenzoanthracene derivative that contains an amino compound group at only one of the 9- and 14-positions of a dibenzo[a,c]anthracene skeleton as represented by the formula (2), the following compounds (1)-m to compounds (42)-m will be shown although the present invention shall not be limited to them.
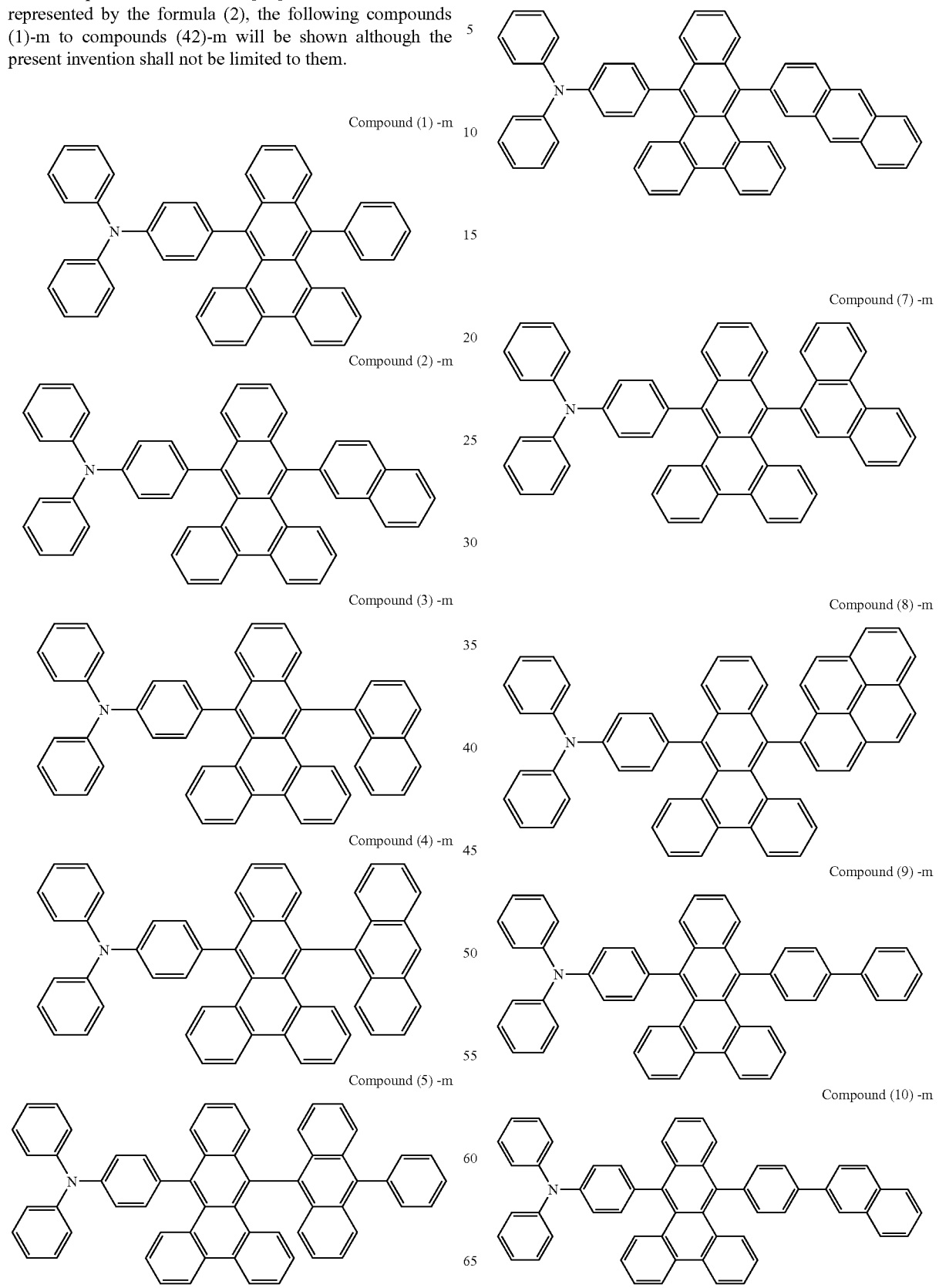

-continued
Compound (11)-m
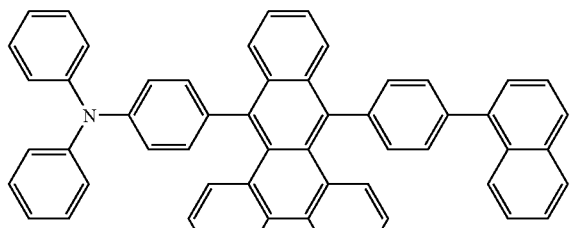
Compound (12)-m
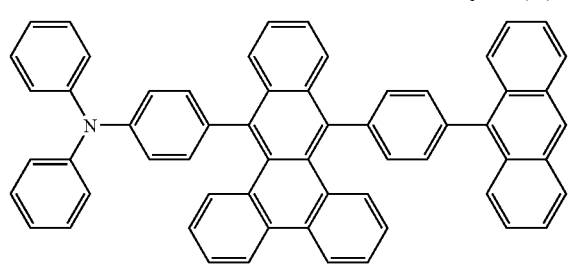
Compound (13)-m
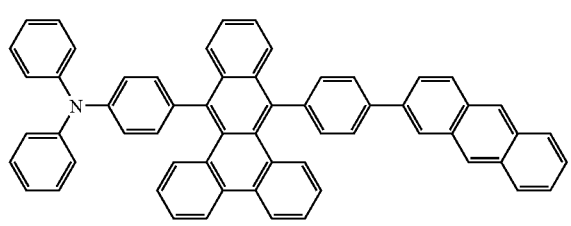
Compound (14)-m
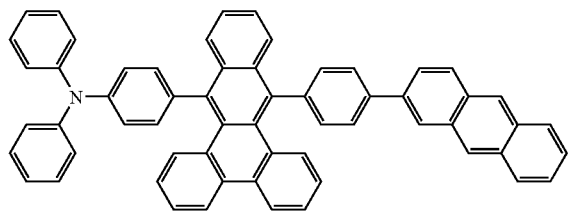
Compound (15)-m
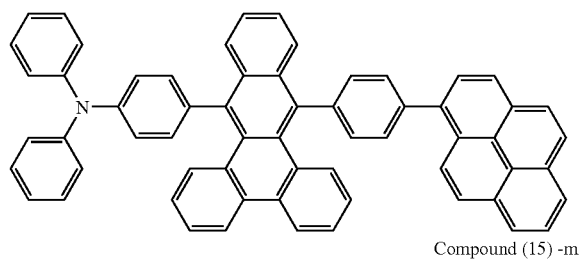
-continued
Compound (16)-m
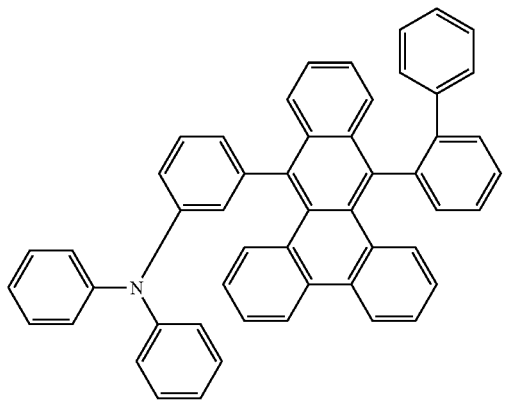
Compound (17)-m
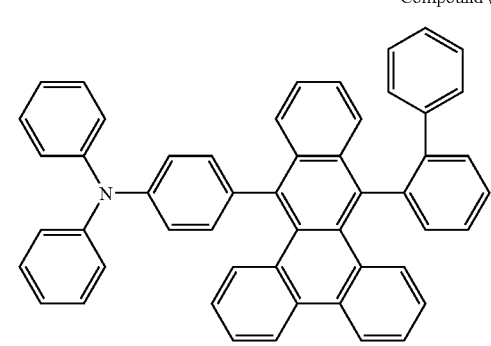
Compound (18)-m
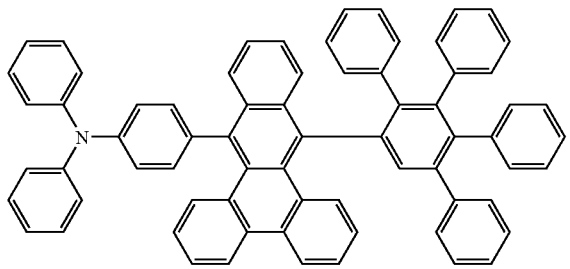
Compound (19)-m
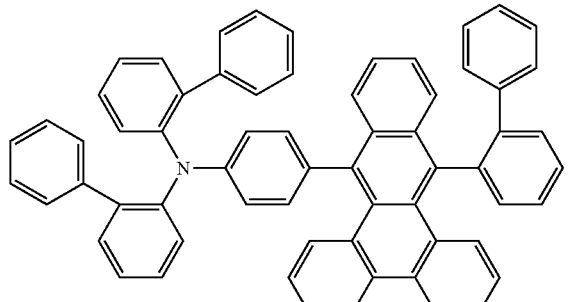
Compound (20)-m
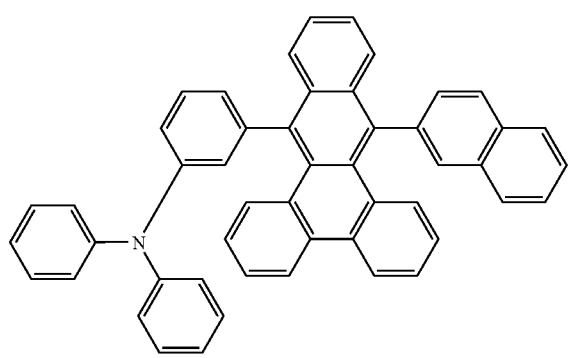

-continued
Compound (21) -m
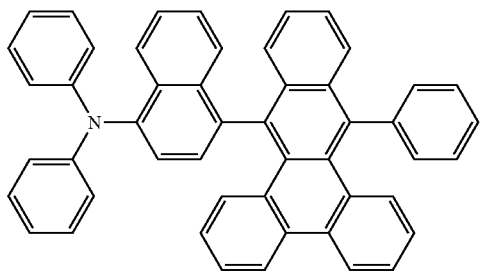
Compound (22) -m
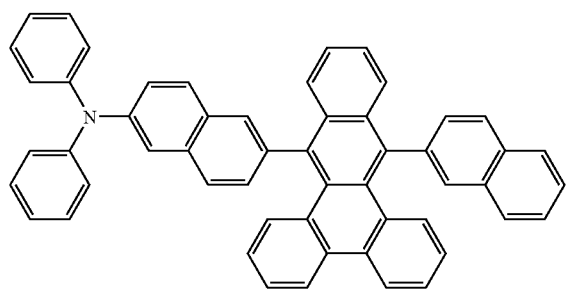
Compound (23) -m
Compound (24) -m
Compound (25) -m
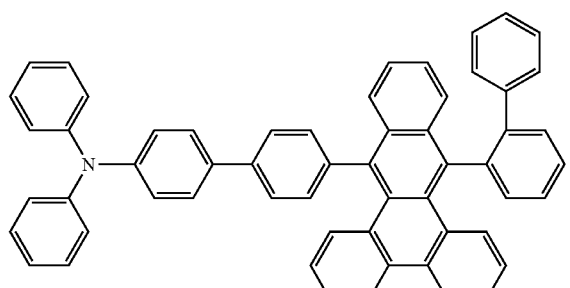
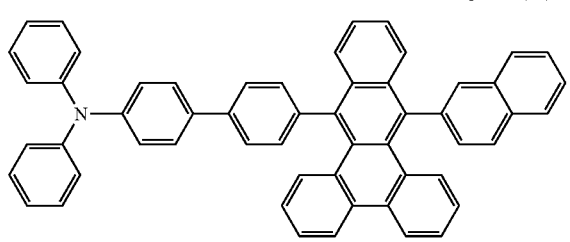
-continued
Compound (26) -m
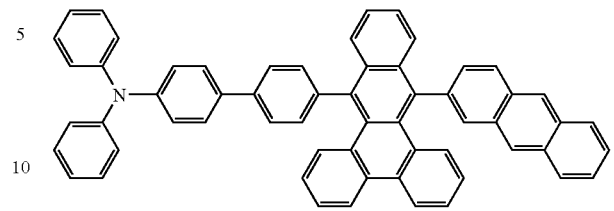
Compound (27) -m
Compound (28) -m
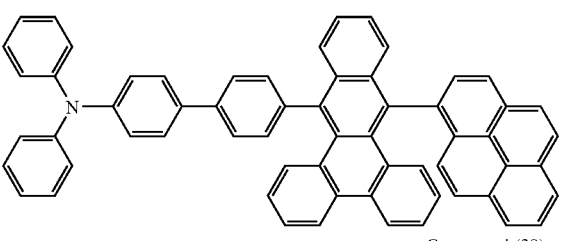
Compound (29) -m
Compound (30) -m
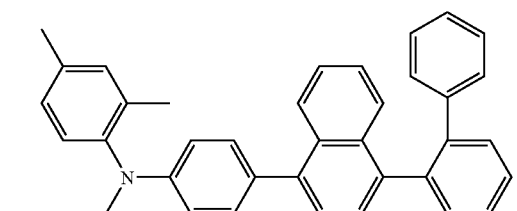

-continued
Compound (31)-m
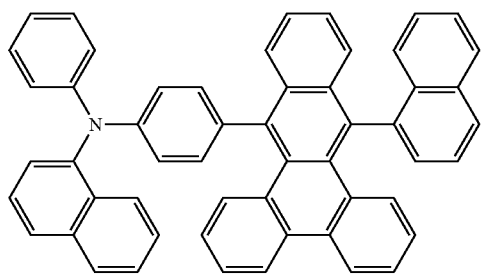
Compound (32)-m
Compound (33)-m
Compound (34)-m
Compound (35)-m
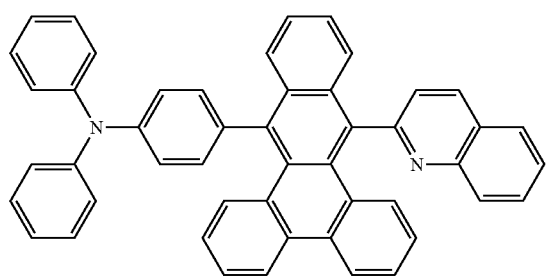
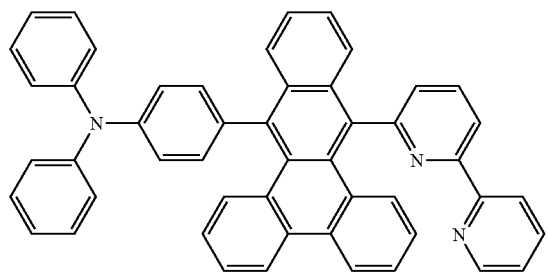
Compound (36)-m
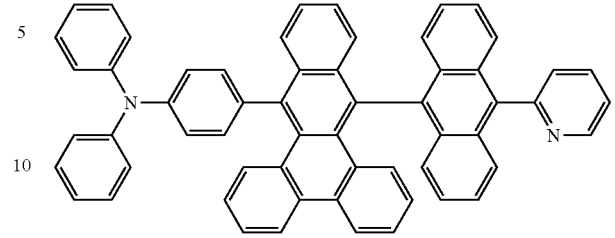
Compound (37)-m
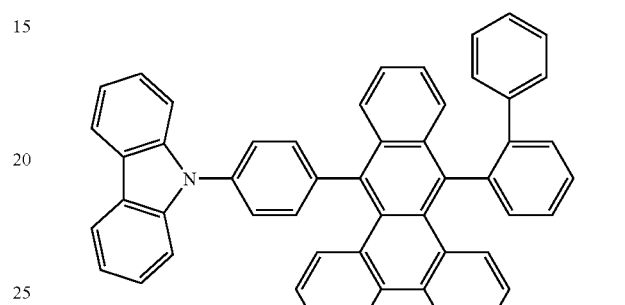
Compound (38)-m
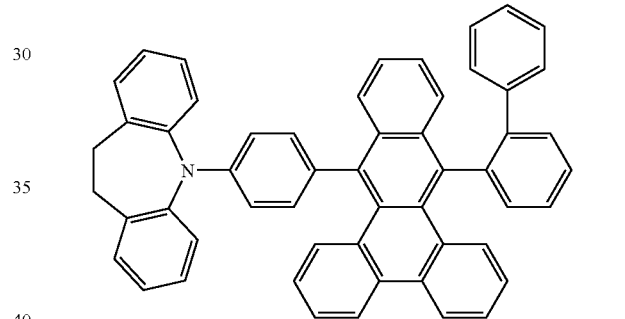
Compound (39)-m
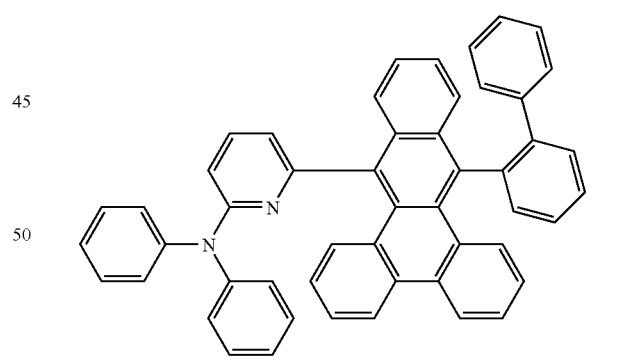
Compound (40)-m
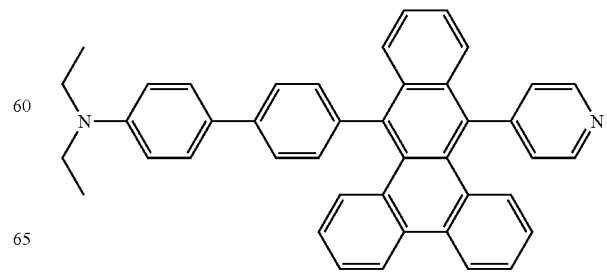

-continued

Compound (41) -m

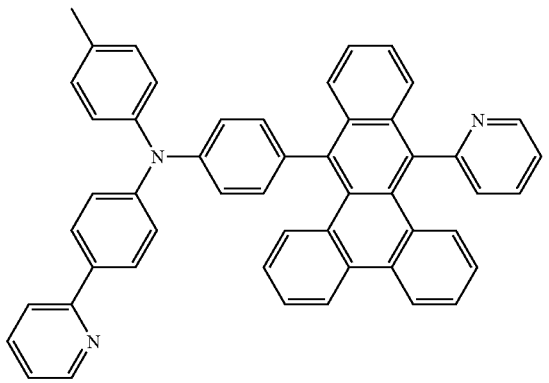

Compound (42) -m

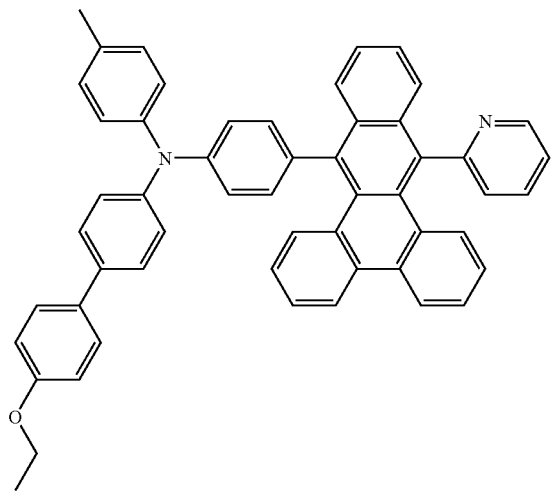

The dibenzoanthracene derivative according to one embodiment of the present invention is useful as a material for forming organic layers in organic electroluminescent devices. It is, therefore, preferred to raise its purity before its provision to a fabrication process of organic electroluminescent devices. A purity of 95% or higher is preferred, with a purity of 99% or higher being more preferred. As a method for obtain an organic compound of such high purity, it is possible to use a known high-purification method, which relies upon sublimation purification, instead of recrystallization, reprecipitation or silica- or alumina-dependent column purification, which is commonly employed as a purification method after the synthesis of an organic compound. Further, a repetition of one of such purification methods or a combination of two or more different ones of such purification methods makes it possible to lower the contents of unreacted substances, reaction byproducts, a catalyst residue, the remaining solvent and the like in the organic light-emitting material according to the present invention and hence to obtain organic electroluminescent devices of still better device characteristics.

<Organic Electroluminescent Devices and Display Apparatus Making Use of Them>

With reference to a drawing, a detailed description will next be made about organic electroluminescent devices making use of the above-described dibenzoanthracene derivative and a display apparatus making use of the organic electroluminescent devices. FIG. 1 is a cross-sectional view schematically illustrating the organic electroluminescent devices according to the present invention and the display apparatus making use of the organic electroluminescent devices.

A display apparatus 1 shown in the drawing is provided with a substrate 2 and an organic electroluminescent device 3 arranged on the substrate 2. The organic electroluminescent device 3 has been formed by stacking a lower electrode 4, an organic layer 5 and an upper electrode 6 one over another on the substrate 2, and is designed to output light from the side of the substrate 2 or from the side of the upper electrode 6. This drawing illustrates a construction that an organic electroluminescent device 3 equivalent to a single pixel is arranged on the substrate 2. It is, however, to be noted that this display apparatus 1 is provided with a plurality of pixels and plural organic electroluminescent devices 3 are arrayed and formed as individual pixels.

The detailed constructions of the individual elements which constitute the display apparatus 1 will next be described in the order of the substrate 2, the lower electrode 4, the upper electrode 6 and the organic layer 5.

The substrate 2 is composed of a glass, silicon or plastic substrate, or a TFT substrate with a TFT (thin film transistor) formed thereon. Especially when the display apparatus 1 is of the transmissive type that light is outputted from the side of the substrate 2, the substrate 2 is supposed to be made of a material having light transmissibility.

The lower electrode 4 formed on the substrate 2 is used as an anode or a cathode. It is to be noted that in the drawing, a case in which the lower electrode 4 is an anode is shown as a typical example.

The lower electrode 4 is supposed to have been patterned in a suitable shape depending upon the drive method for the display apparatus 1. When the drive method for the display apparatus 1 is the simple matrix method, for example, the lower electrode 4 can be formed, for example, into a stripe form. When the drive method for the display apparatus 1 is the active matrix method that the pixels are provided with TFTs, respectively, on the other hand, the lower electrode 4 is formed such that they are formed in a pattern corresponding to the individual ones of the arrayed plural pixels and are connected to the TFTs, which are arranged likewise at the individual pixels, through contact holes (not shown) formed in an interlayer insulating layer covering these TFTs.

On the other hand, the upper electrode 6 arranged above the lower electrode 4 via the organic layer 5 is used as a cathode when the lower electrode 4 is an anode, or is used as an anode when the lower electrode 4 is a cathode. It is to be noted that the drawing illustrates a case in which the upper electrode is a cathode.

When the drive method for the display apparatus 1 is the simple matrix method, the upper electrode 6 is formed as stripes which intersect, for example, the stripes of the lower electrode 4. Organic electroluminescent devices 3 are formed at areas where these strips intersect and stack with each other. When the drive method for the display apparatus 1 is the active matrix method, on the other hand, the upper electrode 6 is formed as a blanket film formed in such a state as covering one side of the substrate 2, and is used as an electrode common to the individual pixels. When the active matrix method is adopted as a drive method for the display apparatus 1, it is desired for the assurance of an aperture ratio of the organic electroluminescent device 3 to construct the display apparatus in the surface-emitting type that light is outputted from the side of the upper electrode 6.

As an anode material for forming the lower electrode 4 (or the upper electrode 6), one having as great a work function as possible is preferred. Preferred examples include nickel, silver, gold, platinum, palladium, selenium, rhodium, ruthenium, iridium, rhenium, tungsten, molybdenum, chromium, tantalum and niobium, and their alloys and oxides; and tin oxide, ITO, zinc oxide, titanium oxide, and the like.

As a cathode material for forming the upper electrode 6 (or the lower electrode 4), on the other hand, one having as small a working function as possible is preferred. Preferred examples include magnesium, calcium, indium, lithium, aluminum, silver, and their alloys.

It is, however, to be noted that, for the electrode adapted to serve as the side from which light produced in the organic electroluminescent device 3 is outputted, a material having light transmissibility should be chosen as desired from the above-mentioned materials and should then be used. In particular, a material capable of transmitting more than 30% of light in the wavelength range of light outputted from the organic electroluminescent device 3 can be used preferably.

When this display apparatus 1 is of the transmissive type that light is outputted from the side of the substrate, for example, an anode material having light transmissibility like ITO is used as the lower electrode 4 which will serve as an anode, and a cathode material having good reflectivity such as aluminum is used as the upper electrode 6 which will serve as a cathode.

When this display apparatus 1 is of the surface-emitting type that light is outputted from the side of the upper electrode, on the other hand, an anode material such as chromium or a silver alloy is used as the lower electrode 4 which will serve as an anode, and a cathode material having light transmissibility such as a magnesium-silver compound (MgAg) is used as the upper electrode 6 which will serve as a cathode. However, the light transmittance of MgAg in the green-color wavelength range is 30% or so. It is, therefore, preferred to design the below-described organic layer 5 such that the construction of a resonator is optimized to output light at a higher intensity.

The organic layer 5, which is held between the lower electrode 4 and the upper electrode 6 as described above, has been formed by stacking a hole transport layer 501, a light-emitting layer 503 and an electron transport layer 505 one over another in this order from the side of the anode (in the drawing, from the side of the lower electrode 4).

As the hole transport layer 501 among these layers, a known material such as NPB [N,N'-bis(1-naphthyl)-N,N'-diphenyl(1,1'-biphenyl)-4,4'-diamine], triphenylamine dimer, trimer or tetramer, or a starburst amine can be used as a single layer or stacked layers, or as a mixture with another adequate known material.

The light-emitting layer 503 arranged on the hole transport layer 501 is the layer characteristic to the present invention, and contains the dibenzoanthracene derivative described above with reference to the formulas (1) and (2), the compounds (1)-d to (46)-d, and the compounds (1)-m to (42)-m. The dibenzoanthracene derivative according to the present invention has high hole transport ability. When the dibenzoanthracene derivative is used singly or at a high concentration of 50 vol. % or higher or is used as a mixture with another material having hole transport ability, an emission of light from the below-described electron transport layer 505 can, therefore, be observed so that the luminescence efficiency in the light-emitting layer 503 itself is lowered. In this case, it is, therefore, preferred to arrange a hole-blocking layer between the light-transmitting layer 503 and the electron transport layer 505.

More preferably, the dibenzoanthracene derivative according to the present invention can be introduced as a guest into the light-transmitting layer 503. The concentration of the dibenzoanthracene derivative in the light-emitting layer 503 is, therefore, lower than 50 vol. %. By controlling its concentration preferably at 1 vol. % or higher but not higher than 40 vol. %, the luminescence brightness and half lifetime of the organic electroluminescent device can be maintained at high values. By controlling its concentration at 1 vol. % or higher but not higher than 20 vol. %, more preferably at 1 vol. % or higher but not higher than 10 vol. %, the luminescence brightness and half lifetime can be maintained at still higher values.

As a host material usable as a mixture with the above-mentioned dibenzoanthracene derivative, it is possible to use a conventionally-known material such as oxadiazole, triazole, benzimidazole, silole, styrylarylene, paraphenylene, spiroparaphenylene or an arylanthracene derivative. As a suited host material, it is desired to choose and use a host material having a fluorescence spectrum which substantially overlaps an absorption spectrum of the dibenzoanthracene derivative employed as a guest material. With the use of such a host material, a more efficient energy transfer takes place from the host material to the gust material, thereby assuring an improvement in luminescence efficiency.

For the electron transport layer 505 arranged on the light-emitting layer 503 of such a construction, it is possible to use a conventionally-known material such as Alq3, oxadiazole, triazole, benzimidazole, or a silole derivative.

In addition to the above-described construction, a hole injection layer may be inserted between the lower electrode 4 as an anode and the hole transport layer 501 although its illustration is omitted in the drawing. As the hole injection layer, a conventionally-known material such as a conductive polymer, e.g., PPV (polyphenylenevinylene), phthalocyanine copper, a starburst amine, or triphenylamine dimer, trimer or tetramer can be used either in the form of a single layer or stacked layers or as a mixture. The insertion of such a hole injection layer is more preferred because the efficiency of an injection can be improved.

Although not shown in the drawing, an electron injection layer may be inserted between the electron transport layer 505 and the cathode (upper electrode) 6. As the electron injection layer, an alkali metal oxide, alkali metal fluoride, alkaline earth metal oxide, alkaline earth metal fluoride or the like, such as lithium oxide, lithium fluoride, cesium iodide or strontium fluoride, can be used. The insertion of such an electron injection layer is more preferred because the efficiency of an injection can be improved.

For the formation of the organic layer 5 of the stacked structure with such materials as described above, the individual organic materials synthesized by processes known in the art can be applied by a known method such as vacuum deposition or spin coating.

To prevent a deterioration of the organic electroluminescent device 3 of such a construction by moisture, oxygen or the like in the atmosphere, it is desired, in the display apparatus 1 equipped with the organic electroluminescent device 3, to form a magnesium fluoride or silicon nitride (SiN) film as a sealing film on the substrate 2 such that the organic electroluminescent device 3 is covered with the sealing film or to apply a sealing cap to the organic electroluminescent device 3 and then to purge a hollow space with dried inert gas or to evacuate the hollow space, although such a sealing film or cap is not shown in the drawing.

Although not shown in the drawing either, the display apparatus 1 equipped with the organic electroluminescent device 3 of such a construction may be designed to perform a full-color display by forming the organic electroluminescent device 3 as a blue-light emitting device at each pixel, arranging a red-light emitting device and a green-light emitting device in combination with the blue-light emitting device at each pixel to construct a single pixel with these light-emitting devices as sub-pixels such that plural pixels, each consisting of these sub-pixels as a single unit, are arrayed on the substrate 2.

In the organic electroluminescent device 3 of the above-described construction, an emission of light in a blue-color wavelength range is obtained with a high luminescence efficiency, a low decrement, high reliability and good color purity owing to the inclusion of the dibenzoanthracene derivative, which has been described above with reference to the formulas (1) and (2), the compounds (1)-d to (46)-d and the compounds (1)-m to (42)-m, in the light-emitting layer 503. The display apparatus 1 equipped with such organic electroluminescent device 3 can, therefore, perform a full-color display with high color reproducibility by combining the organic electroluminescent device 3 with a red-light emitting, organic electroluminescent device and a blue-light emitting, organic electroluminescent device.

In the above-described embodiment, the case that the dibenzoanthracene derivative according to the present invention is used as the light-emitting layer 50 was described by way of example. As the dibenzoanthracene derivative according to the present invention is equipped with high hole transport ability, the dibenzoanthracene derivative may also be used as a material for forming the hole transport layer 501 and the hole injection layer and may also be employed as a doping material for these layers.

EXAMPLES

Synthesis examples of dibenzoanthracene derivatives according to the present invention and examples of organic electroluminescent devices according to the present invention making use of the dibenzoanthracene derivatives of the present invention will next be described specifically. In the following examples, the synthesis examples of the dibenzoanthracene derivatives according to the present invention will be described firstly, fabrication procedures for the organic electroluminescent devices making use of the thus-synthesized dibenzoanthracene derivatives and organic electroluminescent devices of comparative examples will be described next, and then, their evaluation results will be described further.

<Synthesis of Compound (1)-d>

Referring to the following reaction formula (1), 9,14-dibromobenz[a,c]anthracene as a precursor for the target compound was firstly synthesized as will be described next.

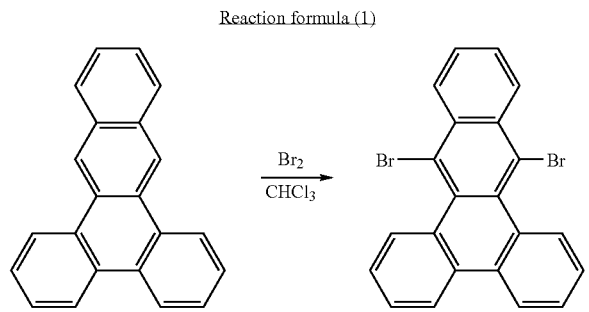

Under a nitrogen atmosphere, dibenzo[a,c]anthracene (10.0 g) was firstly added to chloroform (1 L), and under cooling, bromine (10 g) was added dropwise in four portions into the reaction system. Subsequent to the completion of the dropwise addition, the reaction mixture was stirred at room temperature for 24 hours, and precipitated crystals were collected by filtration. The resulting crystals were washed with water, washed with acetone, and then recrystallized from toluene to obtain 9,14-diboromobenz[a,c]anthracene as a pale yellow solid (12.5 g). Its structure was confirmed by 1H-NMR, 13C-NMR and FD-MS.

Figure 2:
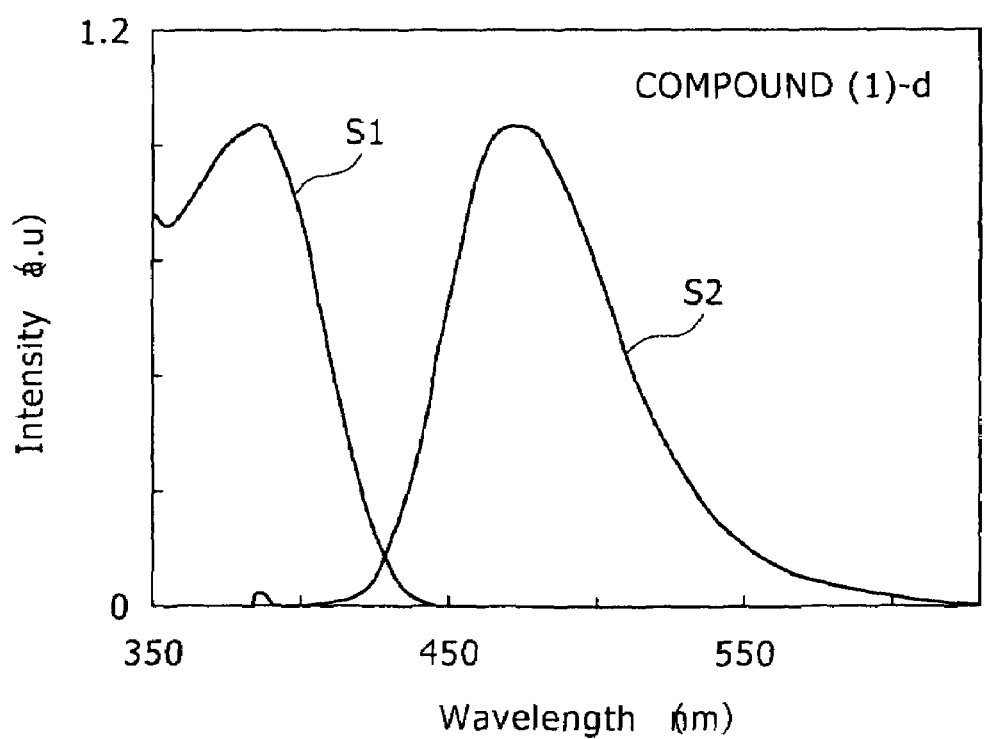
FIG. 2 shows a fluorescence spectrum and absorption spectrum of a compound (1)-d in a dioxane solution.
Figure 3:
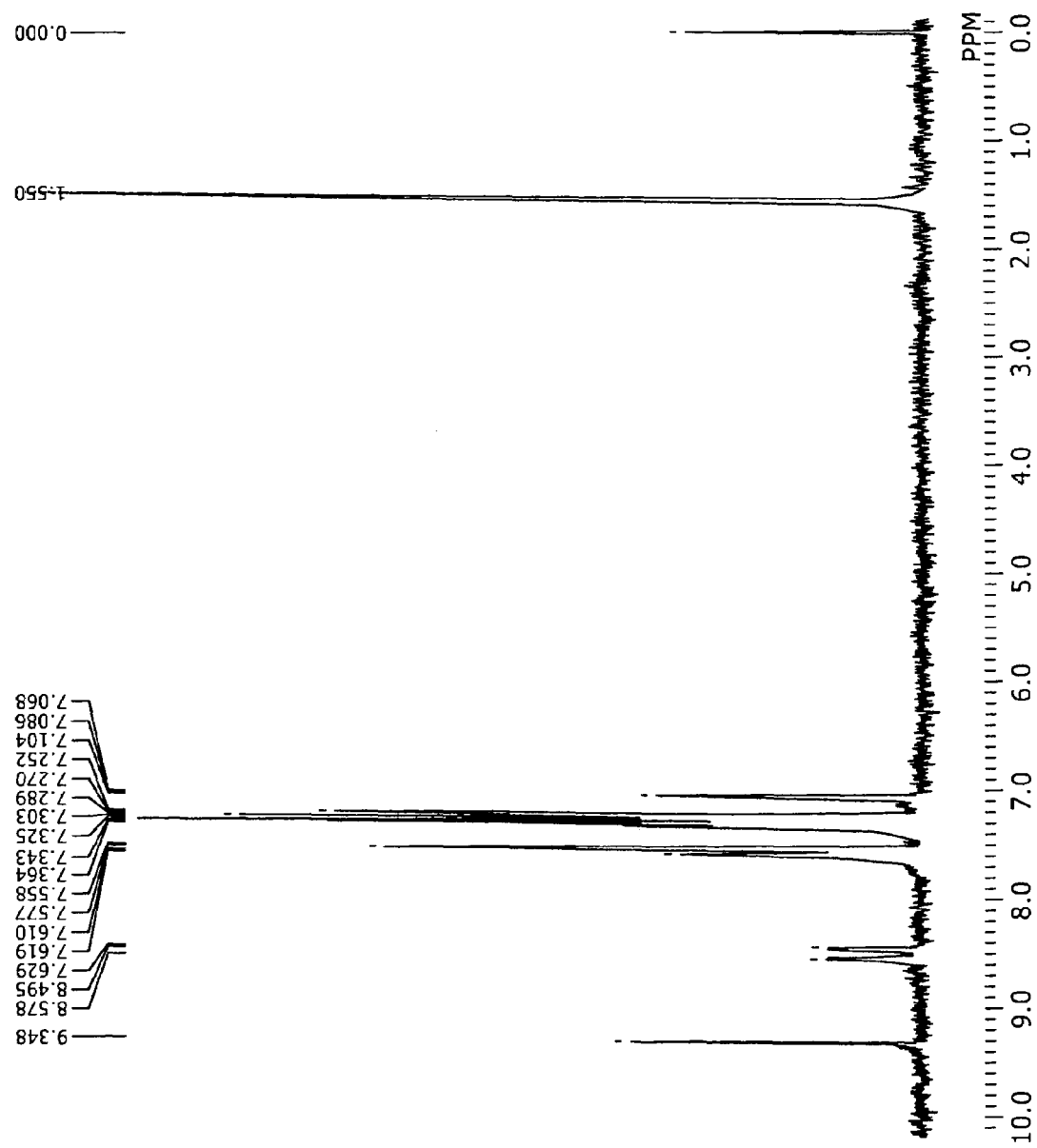
FIG. 3 shows a $^1$H-NMR spectrum of the compound (1)-d obtained by synthesis.

An aliquot (3.0 g) of the resultant 9,14-diboromobenz[a,c]anthracene was next added along with the below-described aromatic borate ester (A1) (5.8 g), sodium hydroxide (1.5 g) and tetrakis(triphenylphosphino)palladium (2.0 g) to dry xylene (200 mL), and under a nitrogen atmosphere, a reaction was conducted at 100° C. for six hours. After completion of the reaction, the resulting precipitate was collected by filtration, washed with water, and suspended in and washed with hot acetone to obtain a yellow powdery compound (2.8 g). By mass spectrometry, a molecular ion peak appeared at m/z=764, which corresponded to the nominal molecular mass of the target compound (1)-d. FIG. 2 shows a fluorescence spectrum s1 and absorption spectrum s2 of the resultant compound (1)-d in a dioxane solution. From the results of $^1$H-NMR as shown in FIG. 3, it was also confirmed that the target compound (1)-d was obtained.

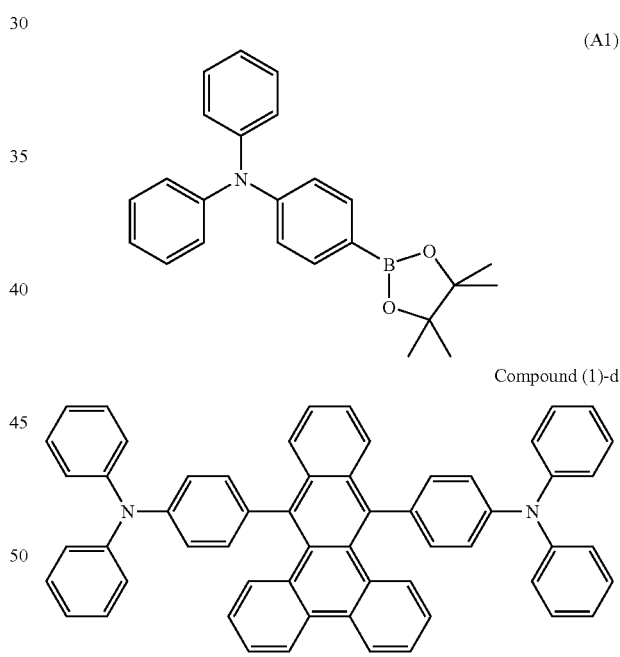

<Synthesis of Compound (2)-d>

Following a similar procedure as in the above-described <Synthesis of the compound (1)-d> except that the aromatic borate ester (A1) was changed to the below-described aromatic borate ester (A2), a synthesis was conducted to obtain a yellow powdery compound (2.5 g). By mass spectrometry, a molecular ion peak appeared at m/z=904, which corresponded to the nominal molecular mass of the target compound (2)-d.

(A2)

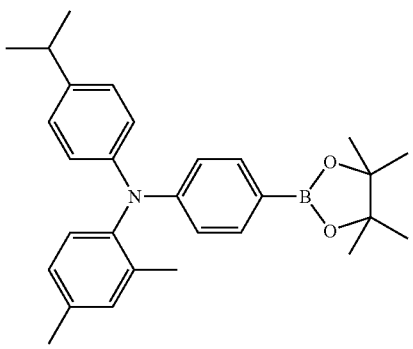

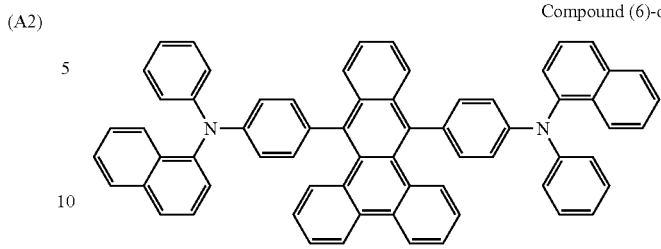

Compound (6)-d

<Synthesis of Compound (9)-d>

Following a similar procedure as in the above-described <Synthesis of the compound (1)-d> except that the aromatic borate ester (A1) was changed to the below-described aromatic borate ester (A4), a synthesis was conducted to obtain a yellow powdery compound (2.5 g). By mass spectrometry, a molecular ion peak appeared at m/z=764, which corresponded to the nominal molecular mass of the target compound (9)-d [2,6-bis{3-(N,N-diphenylamino)phenyl}phenyl]anthracene].

Compound (2)-d

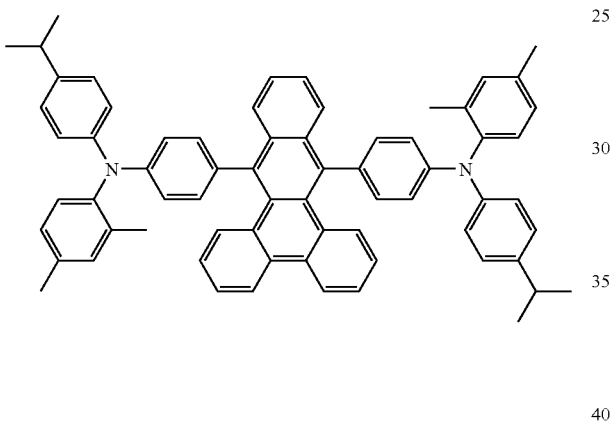

(A4)

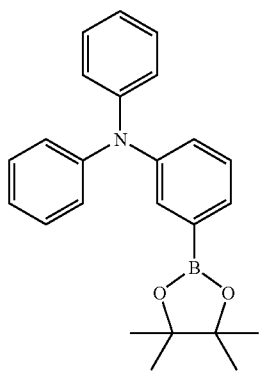

<Synthesis of Compound (6)-d>

Following a similar procedure as in the above-described <Synthesis of the compound (1)-d> except that the aromatic borate ester (A1) was changed to the below-described aromatic borate ester (A3), a synthesis was conducted to obtain a yellow powdery compound (3.4 g). By mass spectrometry, a molecular ion peak appeared at m/z=864, which corresponded to the nominal molecular mass of the target compound (6)-d [2,6-bis{4-(N-(1-naphthyl)-N-phenylamino)phenyl}anthracene].

(A3)

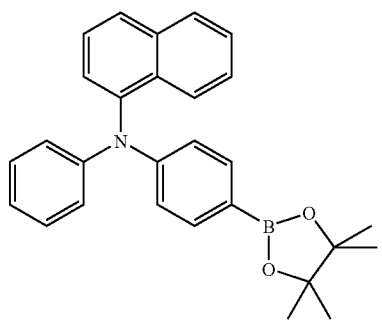

Compound (9)-d

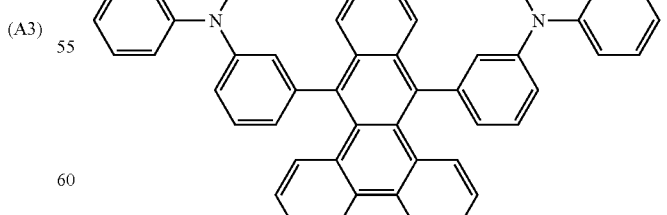

<Synthesis of Compound (16)-d>

Following a similar procedure as in the above-described <Synthesis of the compound (1)-d> except that the aromatic borate ester (A1) was changed to the below-described aromatic borate ester (A5), a synthesis was conducted to obtain a yellow powdery compound (2.5 g). By mass spectrometry, a molecular ion peak appeared at m/z=916, which corresponded to the nominal molecular mass of the target compound (16)-d.

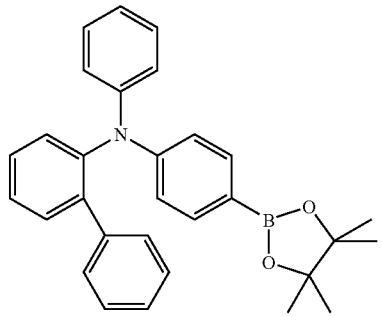

(A5)

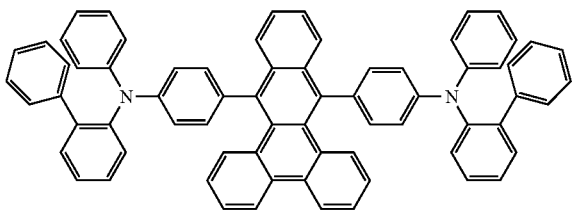

Compound (16)-d

<Synthesis of Compound (25)-d>

Following a similar procedure as in the above-described <Synthesis of the compound (1)-d> except that the aromatic borate ester (A1) was changed to the below-described aromatic borate ester (A6), a synthesis was conducted to obtain a yellow powdery compound (2.5 g). By mass spectrometry, a molecular ion peak appeared at m/z=916, which corresponded to the nominal molecular mass of the target compound (25)-d.

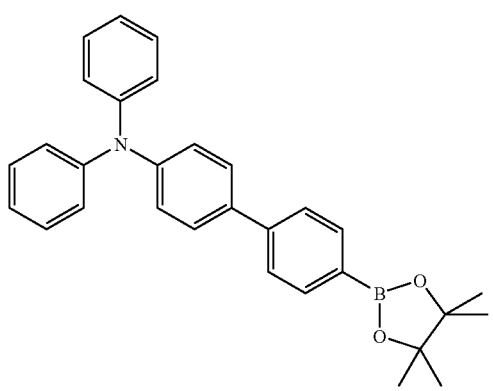

(A6)

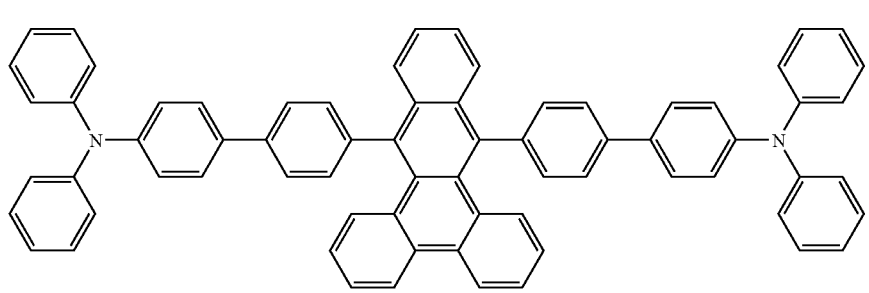

Compound (25)-d

<Synthesis of Compound (2)-m>

In a similar manner as described above with reference to the reaction formula (1), 9,14-dibromobenz[a,c]anthracene as a precursor for the target compound was firstly synthesized.

The resultant 9,14-diboromobenz[a,c]anthracene (3.0 g) was next added along with the below-described aromatic borate ester (A7) (3.0 g), sodium hydroxide (0.5 g) and tetrakis(triphenylphosphino)palladium (0.05 g) to dry xylene (100 mL), and under a nitrogen atmosphere, a reaction was conducted at 100° C. for three hours. After completion of the reaction, the organic layer was separated, washed twice with water, and washed once with a saturated aqueous solution of sodium chloride (hereinafter called "brine"). The thus-washed organic layer was dried over anhydrous sodium sulfate, concentrated under reduced pressure, and then purified by chromatography on a silica gel column to obtain a yellow powdery compound (1.6 g). By mass spectrometry, a molecular ion peak appeared at m/z=599, which corresponded to the nominal molecular mass of the below-described target intermediate (1).

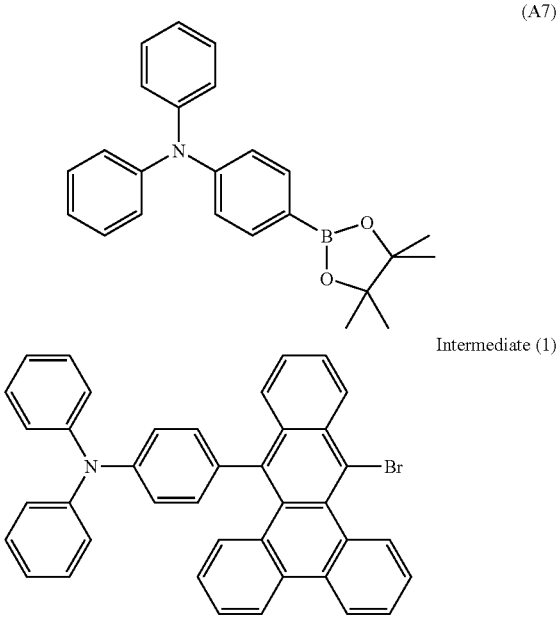

Intermediate (1)

The thus-obtained intermediate (1) (1.6 g) was next added along with the below-described aromatic borate ester (A8) (0.8 g), sodium hydroxide (0.2 g) and tetrakis(triphenylphosphino)palladium (0.05 g) to dry xylene (100 mL), and under a nitrogen atmosphere, a reaction was conducted at 100° C. for six hours. After completion of the reaction, the organic layer was separated, washed twice with water, and washed once with brine. The thus-washed organic layer was dried over anhydrous sodium sulfate, concentrated under reduced pressure, and then purified by chromatography on a silica gel column to obtain a yellow powdery compound (1.1 g). By mass spectrometry, a molecular ion peak appeared at m/z=647, which corresponded to the nominal molecular mass of the below-described target compound (2)-m.

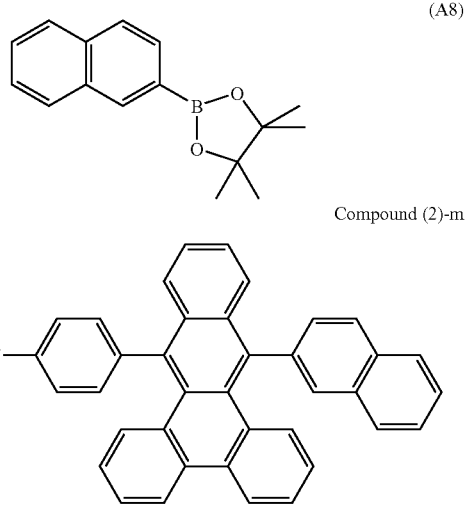

Compound (2)-m

<Synthesis of Compound (5)-m>

Following a similar procedure as in the above-described <Synthesis of the compound (2)-m> except that the aromatic borate ester (A8) was changed to the below-described aromatic borate ester (A9), a synthesis was conducted to obtain a yellow powdery compound (2.5 g). By mass spectrometry, a molecular ion peak appeared at m/z=773, which corresponded to the nominal molecular mass of the target compound (5)-m.

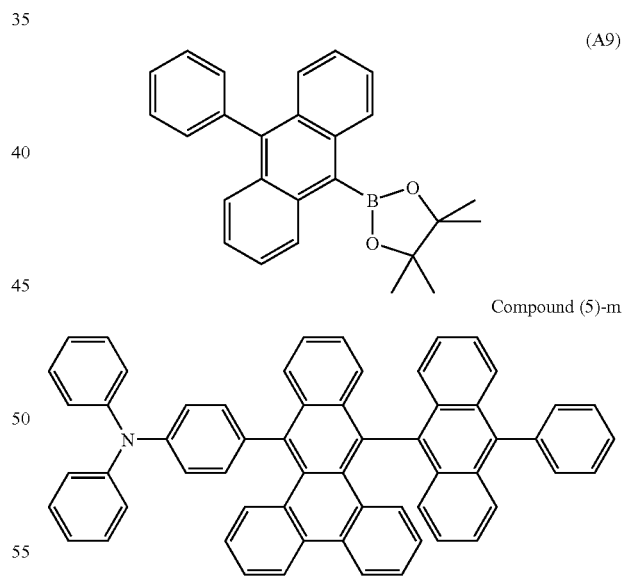

Compound (5)-m

<Synthesis of Compound (17)-m>

Following a similar procedure as in the above-described <Synthesis of the compound (2)-m> except that the aromatic borate ester (A8) was changed to the below-described aromatic borate ester (A10), a synthesis was conducted to obtain a yellow powdery compound (2.5 g). By mass spectrometry, a molecular ion peak appeared at m/z=673, which corresponded to the nominal molecular mass of the target compound (17)-m.

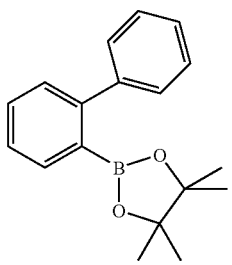

Compound (17)-m

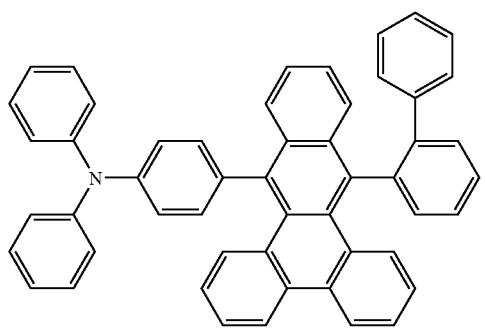

<Synthesis of Compound (23)-m>

Following a similar procedure as in the synthesis of the intermediate (1) in the above-described <Synthesis of the compound (2)-m> except that the aromatic borate ester (A7) was changed to the below-described aromatic borate ester (A11), a synthesis was conducted to obtain a yellow powdery compound (2.0 g). By mass spectrometry, a molecular ion peak appeared at m/z=675, which corresponded to the nominal molecular mass of the below-described intermediate (2).

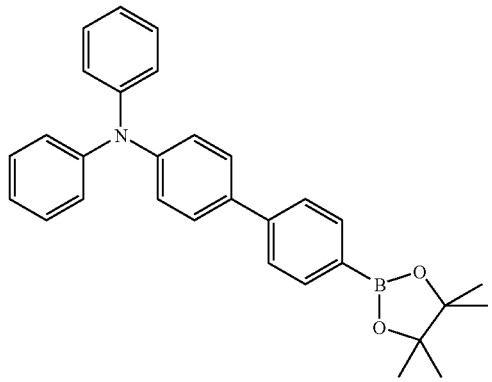

Following a similar procedure as in the synthesis of the <Synthesis of the compound (2)-m> except that the intermediate (1) was changed to the intermediate (2) and the aromatic borate ester (A8) was changed to the below-described aromatic borate ester (A12), a synthesis was conducted to obtain a yellow powdery compound (1.7 g). By mass spectrometry, a molecular ion peak appeared at m/z=749, which corresponded to the nominal molecular mass of the target compound (23)-m.

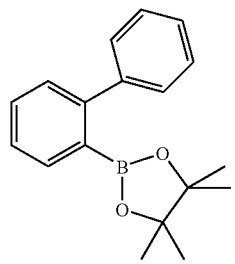

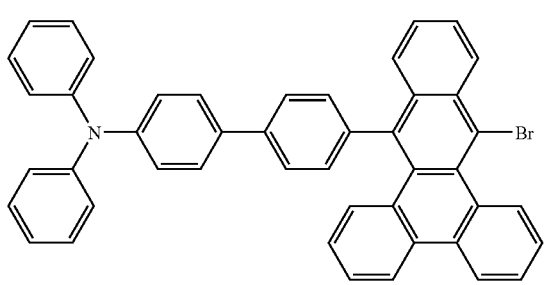

Example 1

Using the compound (1)-d obtained by the above-described synthesis procedure, a transmissive organic electroluminescent device (see FIG. 1) was fabricated as will be described hereinafter.

Firstly, an ITO substrate was prepared with a transparent ITO electrode (anode) of 190 nm film thickness formed as a lower electrode 4 on a glass substrate 2, and was then ultrasonically washed with a neutral detergent, acetone and ethanol. Subsequent to drying the ITO substrate, UV/ozone treatment was conducted for ten minutes. After the ITO substrate was fixed on a substrate holder in a vacuum deposition system, a vacuum chamber was evacuated to $1.4 \times 10^{-4}$ Pa.

On the transparent ITO electrode, the below-described N,N'-bis(1-naphthyl)-N,N'-diphenyl[1,1'-biphenyl]-4,4'-diamine (α-NPD) was firstly deposited at a deposition rate of 0.2 nm/sec to a thickness of 65 nm to form a hole injection layer 501.

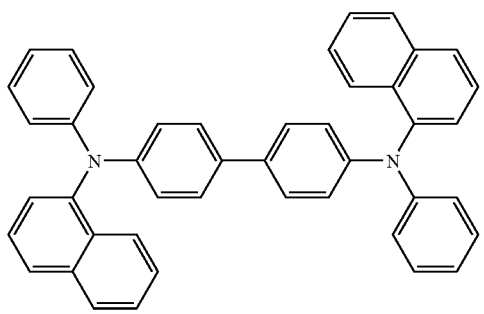

α-NPD

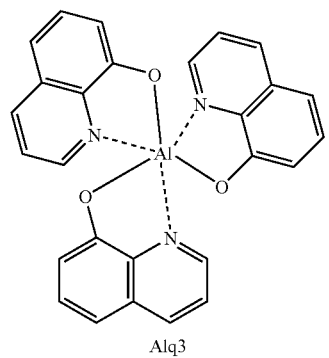

Alq3

Using the below-described 9,10-di(2-naphthyl)anthracene (ADN) as a host and the below-described compound (1)-d as a guest, respectively, they were then codeposited from different evaporation sources at a total deposition rate of about 0.2 nm/sec to a thickness of 35 nm to form a light-emitting layer 503 having a guest concentration of 10 vol. %.

ADN

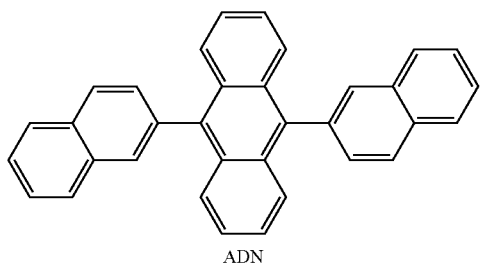

Compound (1)-d

The below-described Alq3 was next deposited at a deposition rate of 0.2 nm/sec to a thickness of 18 nm to form an electron transport layer 505. Over the electron transport layer 505, lithium fluoride (LiF) was deposited to a thickness of 0.1 nm, and further, magnesium and silver were codeposited at a total deposition rate of about 0.4 nm/sec to a thickness of about 70 nm (atomic ratio: Mg/Ag=95/5) to form a cathode (upper electrode 6), so that a bottom-emitting electroluminescent device 3 in which an emission of light is outputted from the side of the lower electrode 4 was fabricated.

When the thus-fabricated organic electroluminescent device was driven by a DC current at a current density of 25 mA/cm$^2$, a) the drive voltage was 5.7 V, the luminescence efficiency was 3.8 cd/A, and the power efficiency was 2.01 m/W. Further, a blue light emission of b) luminescence brightness=1,050 cd/m$^2$ and c) luminescence peak=471 nm was confirmed. When the electroluminescent device was driven by a constant current at an initial brightness of 1,500 cd/m$^2$, d) its half lifetime (the lifetime until the brightness was reduced to a half) was 1,200 hours.

Examples 2-9

In a similar manner as the above-described fabrication procedure of the organic electroluminescent device of Example 1 except that the compounds described below in Table 1 were separately used as guest materials in place of the guest consisting of the dibenzoanthracene derivative as the compound (1)-d in the light-emitting layer 503, bottom-emitting organic electroluminescent devices 3 were fabricated, respectively. It is to be noted that the concentration of the guest in each light-emitting layer 503 was controlled at 10 vol. %.

TABLE 1

| | Guest material in light-emitting layer | a) Drive voltage (V) | b) Luminescence brightness (cd/m$^2$) | c) Color of emitted light | d) Light-emitting lifetime (hr) |
|---|---|---|---|---|---|
| Example 1 | Compound(1)-d | 5.7 | 1,050 | Blue | 1,200 |
| Example 2 | Compound(2)-d | 5.6 | 1,160 | Blue | 1,350 |
| Example 3 | Compound(6)-d | 5.6 | 1,150 | Blue | 1,300 |
| Example 4 | Compound(9)-d | 6.1 | 950 | Blue | 1,050 |
| Example 5 | Compound(16)-d | 5.6 | 1,150 | Blue | 1,300 |
| Example 6 | Compound(19)-d | 6.2 | 980 | Blue | 1,080 |
| Example 7 | Compound(21)-d | 6.0 | 1,100 | Blue | 1,150 |
| Example 8 | Compound(29)-d | 5.9 | 990 | Blue | 1,050 |
| Example 9 | Compound(37)-d | 5.9 | 950 | Blue | 1,100 |
| Comp. Ex. 1 | BCzVBi 5% | 6.5 | 850 | Blue | 390 |

With respect to the organic electroluminescent devices of Examples 2-9 fabricated as described above, measurements were performed as in Example 1. The results a) to d) are also shown above in Table 1.

It is to be noted that the individual compounds (dibenzoanthracene derivatives) were synthesized by replacing the aromatic borate ester (A1), which was used in the above-described <Synthesis of the compound (1)-d>, with aromatic borate esters (the borate esters of amino compounds) to be bonded to the 9- and 14-positions of the dibenzo[a,c]anthracene derivative, respectively.

Comparative Example 1

In a similar manner as the above-described fabrication procedure of the organic electroluminescent device of Example 1 except that the below-described BCzVBi, which is disclosed as a guest material for a blue emission in Non-patent Document 2, was used in place of the guest consisting of the dibenzoanthracene derivative as the compound (1)-d in the light-emitting layer 503, an organic electroluminescent device was fabricated. It is to be noted that the concentration of the guest was controlled at 5 vol. %.

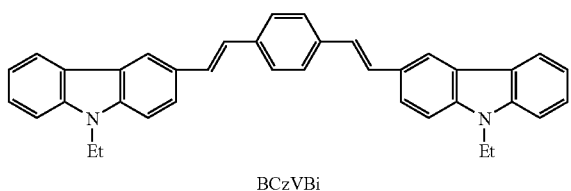

BCzVBi

With respect to the organic electroluminescent device of Comparative Example 1 fabricated as described above, measurements were performed as in Example 1. The results a) to d) are also shown above in Table 1.

<Assessment Results 1>

As shown above in Table 1, it has been confirmed that an emission of blue light is available from each of the electroluminescent devices of Examples 1-9 in each of which the corresponding dibenzoanthracene derivative [the compound (1)-d or the like] according to the present invention, said dibenzoanthracene derivative containing its corresponding amino compound groups substituted to both the 9- and 14-positions of a dibenzo[a,c]anthracene skeleton, was used as a light-emitting material. Further, the electroluminescent devices of Examples 1-9 each demonstrated a luminescence brightness higher than 950 cd/m$^2$ and a half lifetime longer than 1,050 hours.

In contrast, with the organic electroluminescent device of Comparative Example 1 in which the above-described BCzVBi disclosed as a guest material for a blue emission in Non-patent Document 2 was used as a light-emitting material, the half lifetime was as short as 390 hours although a blue emission was obtained.

It has been confirmed from the foregoing that dibenzoanthracene derivatives according to one embodiment of the present invention, each of which contains amino compound groups substituted to both the 9- and 14-positions of a dibenzo[a,c]anthracene skeleton, are excellent in both luminescence efficiency and service life characteristics as blue-light emitting materials in organic electroluminescent devices.

Examples 10-14

In a similar manner as the above-described fabrication procedure of the organic electroluminescent device of Example 1 except that the concentration of the guest consisting of the dibenzoanthracene derivative as the compound (1)-d in the light-emitting layer 503 was controlled at 1 vol. %, 10 vol. %, 20 vol. %, 40 vol. % and 50 vol. %, respectively, transmissive organic electroluminescent devices 3 were fabricated.

With respect to the above-fabricated respective organic electroluminescent devices, measurements were performed for a) drive voltage, b) luminescence brightness, c) the color of emitted light and d) half lifetime as in Example 1. The results are shown below in Table 2. In addition, the above-described results of Comparative Example 1 are also shown in Table 2.

TABLE 2

| | Guest material in light-emitting layer | a) Drive voltage (V) | b) Luminescence brightness (cd/m$^2$) | c) Color of emitted light | d) Light-emitting lifetime (hr) |
|---|---|---|---|---|---|
| Example 10 | Compound(1)-d 1% | 5.8 | 980 | Blue | 1,100 |
| Example 11 | Compound(1)-d 10% | 5.7 | 1,050 | Blue | 1,200 |
| Example 12 | Compound(1)-d 20% | 5.1 | 930 | Blue | 1,050 |
| Example 13 | Compound(1)-d 40% | 4.8 | 880 | Blue | 960 |
| Example 14 | Compound(1)-d 50% | 4.5 | 750 | Blue | 890 |
| Comp. Ex. 1 | BCzVBi 5% | 6.5 | 850 | Blue | 390 |

<<Assessment Results 2>>

From the results shown in Table 2, it is appreciated that the control of the concentration of a dibenzoanthracene derivative according to one embodiment of the present invention, which contains amino compound groups substituted to both the 9- and 14-positions of a dibenzo[a,c]anthracene skeleton, at 1 vol. % or higher but not higher than 40 vol. % in a light-emitting layer 503 makes it possible to maintain b) a luminance brightness and d) a half lifetime at values higher than the corresponding values of Comparative Example 1, respectively. It has also been confirmed that the control of the concentration preferably at 1 vol. % or higher but not higher than 20 vol. %, more preferably at 10 vol. % or so makes it possible to maintain b) a luminance brightness and d) a half lifetime at still higher values, respectively.

Example 15

In this example, a surface-emitting electroluminescent device was fabricated using a dibenzoanthracene derivative according to one embodiment of the present invention which contained amino compound groups substituted to both the 9- and 14-positions of a dibenzo[a,c]anthracene skeleton.

A transparent ITO electrode (anode) of 11 nm film thickness was formed and stacked as a lower electrode 4 on a glass substrate 2 via a Ag alloy layer of 190 nm film thickness, and was then ultrasonically washed with a neutral detergent, acetone and ethanol. Subsequent to drying, UV/ozone treatment was conducted for 10 minutes. After the substrate was fixed on a substrate holder in a vacuum deposition system, a vacuum chamber was evacuated to 1×10$^{-6}$ Torr.

In the evacuated state, the above-described α-NPD was firstly deposited at a deposition rate of 0.2 nm/sec to a thickness of 24 nm on the transparent ITO electrode to form a hole transport layer 501. Using the above-described ADN as a host and the above-described compound (1)-d as a guest, respectively, they were then codeposited from different evaporation sources at a total deposition rate of about 0.2 nm/sec to a thickness of 35 nm to form a light-emitting layer 503 having a guest concentration of 10 vol. %. The above-described Alq3 was next deposited at a deposition rate of 0.2 nm/sec to a thickness of 18 nm to form an electron transport layer 505. Over the electron transport layer 505, lithium fluoride (LiF) was deposited to a thickness of 0.1 nm, and further, magnesium and silver were codeposited at a total deposition rate of about 0.4 nm/sec to a thickness of about 12 nm (atomic ratio: Mg/Ag=95/5) to form a cathode (upper electrode 6), so that a surface-emitting electroluminescent device 3 in which an emission of light is outputted from the side of the upper electrode 6 was fabricated.

When the thus-fabricated organic electroluminescent device was driven by a DC current at a current density of 25 mA/cm$^2$, a) the drive voltage was 4.6 V, the luminescence efficiency was 2.0 cd/A, and the power efficiency was 2.11 m/W. Further, a blue emission of b) luminescence brightness=687 cd/m$^2$ and c) luminescence peak=468 nm was confirmed. As a result, it has been confirmed that even with a surface-emitting organic electroluminescent device, the use of the dibenzoanthracene derivative according to the present invention, which contains amino compound groups substituted to both the 9- and 14-positoins of a dibenzo[a,c]anthracene skeleton, as a light-emitting material makes it possible to obtain an emission of blue light.

Examples 16-24

In a similar manner as the above-described fabrication procedure of the organic electroluminescent device of Example 1 except that the compounds (dibenzoanthracene derivatives), each of which is described below in Table 3 and contained only one amino compound group, were separately used as guest materials in place of the guest consisting of the dibenzoanthracene derivative as the compound (1)-d in the light-emitting layer 503, bottom-emitting organic electroluminescent devices 3 were fabricated, respectively. It is to be noted that the concentration of the guest in each light-emitting layer 503 was controlled at 10 vol. %.

TABLE 3

| | Guest material in light-emitting layer | a) Drive voltage (V) | b) Luminescence brightness (cd/m$^2$) | c) Color of emitted light | d) Light-emitting lifetime (hr) |
|---|---|---|---|---|---|
| Example 16 | Compound(2)-m | 5.8 | 990 | Blue | 1,030 |
| Example 17 | Compound(5)-m | 5.8 | 1,030 | Blue | 1,050 |
| Example 18 | Compound(8)-m | 5.6 | 1,100 | Blue | 980 |
| Example 19 | Compound(9)-m | 6.1 | 950 | Blue | 990 |
| Example 20 | Compound(15)-m | 6.3 | 890 | Blue | 860 |
| Example 21 | Compound(17)-m | 5.5 | 1,150 | Blue | 1,150 |
| Example 22 | Compound(23)-m | 5.7 | 960 | Blue | 960 |
| Example 23 | Compound(24)-m | 5.7 | 930 | Blue | 980 |
| Example 24 | Compound(25)-m | 5.6 | 1,160 | Blue | 1,350 |
| Comp. Ex. 1 | BCzVBi 5% | 6.5 | 850 | Blue | 390 |

With respect to the organic electroluminescent devices of Examples 16-24 fabricated as described above, measurements were performed as in Example 1. The results a) to d) are also shown above in Table 3. In addition, the results of Comparative Example 1 are also shown.

It is to be noted that the individual compounds (dibenzoanthracene derivatives) were synthesized by replacing the aromatic borate esters (A7) (A8), which were used in the above-described <Synthesis of the compound (2)-m>, with aromatic borate esters (one of which was the borate ester of an amino compound) to be bonded to the 9- and 14-positions of the dibenzo[a,c]anthracene derivative, respectively.

<<Assessment Results 3>>

As shown above in Table 3, it has been confirmed that an emission of blue light is available from each of the electroluminescent devices of Examples 16-24 in each of which the corresponding dibenzoanthracene derivative [the compound (2)-m or the like] according to the present invention, said dibenzoanthracene derivative containing its corresponding amino compound group substituted to only one of the 9- and 14-positions of a dibenzo[a,c]anthracene skeleton, was used as a light-emitting material. Further, the electroluminescent devices of Examples 16-24 each demonstrated a luminescence brightness higher than 890 cd/m$^2$ and a half lifetime longer than 860 hours. These values were greater than the results of Comparative Example 1.

It has been confirmed from the foregoing that dibenzoanthracene derivatives according to the present invention, each of which contains an amino compound group substituted to only one of the 9- and 14-positions of a dibenzo[a,c]anthracene skeleton, are excellent in both luminescence efficiency and service life characteristics as blue-light emitting materials in organic electroluminescent devices.

Examples 25-29

In a similar manner as the above-described fabrication procedure of the organic electroluminescent device of Example 16 except that the concentration of the guest consisting of the dibenzoanthracene derivative as the compound (2)-m in the light-emitting layer 503 was controlled at 1 vol. %, 10 vol. %, 20 vol. %, 40 vol. % and 50 vol. %, respectively, bottom-emitting organic electroluminescent devices 3 were fabricated.

With respect to the above-fabricated respective organic electroluminescent devices, measurements were performed for a) drive voltage, b) luminescence brightness, c) the color of emitted light and d) half lifetime as in Example 1. The results are shown below in Table 4. In addition, the above-described results of Comparative Example 1 are also shown in Table 4.

TABLE 4

| | Guest material in light-emitting layer | a) Drive voltage (V) | b) Luminescence brightness (cd/m$^2$) | c) Color of emitted light | d) Light-emitting lifetime (hr) |
|---|---|---|---|---|---|
| Example 25 | Compound(2)-m 1% | 6.0 | 950 | Blue | 1,000 |
| Example 26 | Compound(2)-m 10% | 5.8 | 990 | Blue | 1,030 |
| Example 27 | Compound(2)-m 20% | 5.6 | 930 | Blue | 960 |
| Example 28 | Compound(2)-m 40% | 5.4 | 870 | Blue | 900 |
| Example 29 | Compound(2)-m 50% | 4.8 | 770 | Blue | 830 |
| Comp. Ex. 1 | BCzVBi 5% | 6.5 | 850 | Blue | 390 |

<<Assessment Results 4>>

From the results shown in Table 4, it is appreciated that the control of the concentration of a dibenzoanthracene derivative according to the present invention, which contains an amino compound group substituted to only one of the 9- and 14-positions of a dibenzo[a,c]anthracene skeleton, at 1 vol. % or higher but not higher than 40 vol. % in a light-emitting layer 503 makes it possible to maintain b) a luminance brightness and d) a half lifetime at values higher than the corresponding values of Comparative Example 1, respectively. It has also been confirmed that the control of the concentration preferably at 1 vol. % or higher but not higher than 20 vol. %, more preferably at 10 vol. % or so makes it possible to maintain b) a luminance brightness and d) a half lifetime at still higher values, respectively.

Example 30

In this example, a surface-emitting electroluminescent device was fabricated using a dibenzoanthracene derivative according to the present invention which contained an amino compound group substituted to only one of the 9- and 14-positions of a dibenzo[a,c]anthracene skeleton.

Described specifically, in a similar manner as the above-described fabrication procedure of the organic electroluminescent device of Example 15 except that the compound 7-(m) was used as a guest material in place of the guest consisting of the dibenzoanthracene derivative as the compound (1)-d in the light-emitting layer 503, the surface-emitting organic electroluminescent devices 3 was fabricated. It is to be noted that the concentration of the guest in the light-emitting layer 503 was controlled at 10 vol. %.

When the thus-fabricated organic electroluminescent device was driven by a DC current at a current density of 25 mA/cm$^2$, a) the drive voltage was 4.6 V, the luminescence efficiency was 2.0 cd/A, and the power efficiency was 2.11 m/W. Further, a blue light emission of b) luminescence brightness=687 cd/m$^2$ and c) luminescence peak=467 nm was confirmed. As a result, it has been confirmed that even with a surface-emitting organic electroluminescent device, the use of the dibenzoanthracene derivative according to one embodiment of the present invention, which contains an amino compound group substituted to only one of the 9- and 14-positoins of a dibenzo[a,c]anthracene skeleton, as a light-emitting material makes it possible to obtain an emission of blue light.

While preferred embodiments of the present invention have been described using specific terms, such description is for illustrative purpose only, and it is to be understood that changes and variations may be made without departing from the spirit or scope of the following claims.

What is claimed is:

1. A dibenzoanthracene derivative substituted by an amino compound group at least one of 9-position and 14-position of a dibenzo[a,c]anthracene skeleton and represented by the following formula (1) or (2):

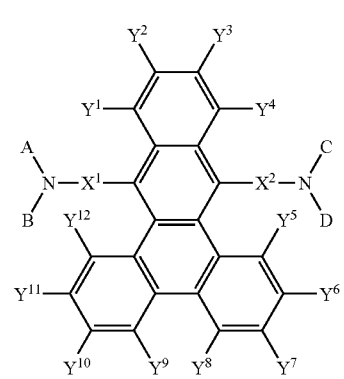

Formula (1)

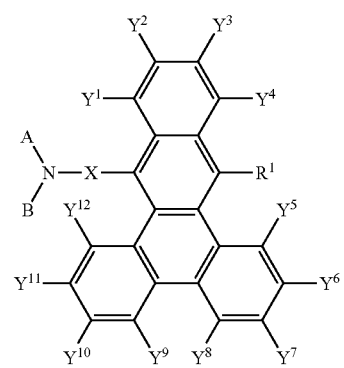

Formula (2)

wherein:
$X^1$, $X^2$ and X each independently represents a substituted or unsubstituted arylene group or a substituted or unsubstituted divalent heterocyclic group;

A, B, C and D each independently represents a substituted or unsubstituted alkyl group, a substituted or unsubstituted aryl group or a substituted or unsubstituted heterocyclic group, and between the adjacent groups, may be fused together to form rings; and $Y^1$ to $Y^{12}$ and $R^1$ each independently represents a hydrogen atom, a halogen atom, a substituted or unsubstituted alkyl group, an alkoxy group, a substituted or unsubstituted aryl group, or a substituted or unsubstituted heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings.

2. The dibenzoanthracene derivative according to claim 1, wherein:
$X^1$, $X^2$ and X each independently represents a substituted or unsubstituted C6-28 arylene group or a substituted or unsubstituted divalent C5-21 heterocyclic group;

A, B, C and D each independently represents a substituted or unsubstituted C1-20 alkyl group, a substituted or unsubstituted C6-28 aryl group or a substituted or unsubstituted C5-21 heterocyclic group, and between the adjacent groups, may be fused together to form rings; and $Y^1$ to $Y^{12}$ and $R^1$ each independently represents a hydrogen atom, a halogen atom, a substituted or unsubstituted C1-20 alkyl group, an C1-20 alkoxy group, a substituted or unsubstituted C6-28 aryl group, or a substituted or unsubstituted C5-21 heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings.

3. The dibenzoanthracene derivative according to claim 1, wherein:
$X^1$, $X^2$ and X each independently represents a substituted or unsubstituted C6-18 arylene group or a substituted or unsubstituted divalent C5-17 heterocyclic group; and
A, B, C and D each independently represents a substituted or unsubstituted, linear, branched or cyclic, C1-20 alkyl group, a substituted or unsubstituted C6-18 aryl group or a substituted or unsubstituted C5-17 heterocyclic group, and between the adjacent groups, may be fused together to form rings.

4. The dibenzoanthracene derivative according to claim 1, wherein $X^1$, $X^2$ and X are each independently a substituted or unsubstituted phenylene group.

5. The dibenzoanthracene derivative according to claim 1, wherein $Y^1$ to $Y^{12}$ and $R^1$ are each a hydrogen atom.

6. An organic electroluminescent device with an organic layer, which has at least a light-emitting layer, held between a pair of electrodes, wherein said organic layer is comprised of:
a dibenzoanthracene derivative substituted by an amino compound group at least one of 9-position and 14-position of a dibenzo[a,c]anthracene skeleton and represented by the following formula (1) or (2):

Formula (1)

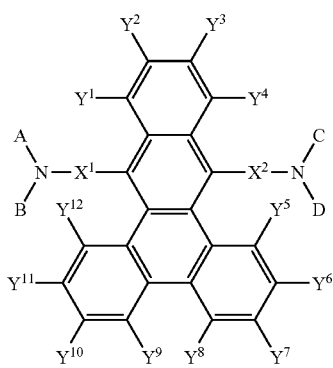

Formula (2)

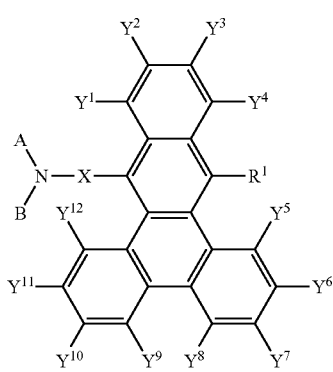

wherein:
$X^1$, $X^2$ and X each represents substituted or unsubstituted arylene group or a substituted or unsubstituted divalent heterocyclic group;
A, B, C and D each independently represents a substituted or unsubstituted alkyl group, a substituted or unsubstituted aryl group or a substituted or unsubstituted heterocyclic group, and between the adjacent groups, may be fused together to form rings; and
$Y^1$ to $Y^{12}$ and $R^1$ each independently represents a hydrogen atom, a halogen atom, a substituted or unsubstituted alkyl group, an alkoxy group, a substituted or unsubstituted aryl group, or a substituted or unsubstituted heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings.

7. The organic electroluminescent device according to claim 6, wherein said dibenzoanthracene derivative is used as a material that forms said light-emitting layer.

8. The organic electroluminescent device according to claim 7, wherein said dibenzoanthracene derivative is used as a light-emitting material.

9. The organic electroluminescent device according to claim 8, wherein said dibenzoanthracene derivative is used as a blue-light emitting material.

10. The organic electroluminescent device according to claim 8, wherein said light-emitting layer contains not more than 40 vol. % of said dibenzoanthracene derivative.

11. The organic electroluminescent device according to claim 6, wherein said dibenzoanthracene derivative is used as a hole injection material or a hole transport material in said organic layer.

12. A display apparatus comprising:
a plurality of organic electroluminescent devices formed in an array on a substrate, each of said organic electroluminescent devices being provided with an organic layer, which has at least a light-emitting layer, held between an anode and a cathode, wherein
at least one organic electroluminescent device is comprised of:
a dibenzoanthracene derivative substituted by an amino compound group at least one of 9-position and 14-position of a dibenzo[a,c]anthracene skeleton and represented by the following formula (1) or (2):

Formula (1)

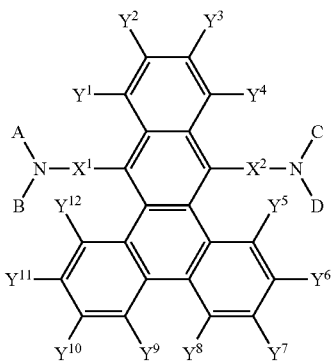

Formula (2)

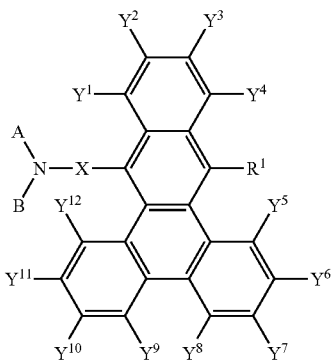

wherein:

$X^1$, $X^2$ and X each independently represents a substituted or unsubstituted arylene group or a substituted or unsubstituted divalent heterocyclic group;

A, B, C and D each independently represents a substituted or unsubstituted alkyl group, a substituted or unsubstituted aryl group or a substituted or unsubstituted heterocyclic group, and between the adjacent groups, may be fused together to form rings; and $Y^1$ to $Y^{12}$ and $R^1$ each independently represents a hydrogen atom, a halogen atom, a substituted or unsubstituted alkyl group, an alkoxy group, a substituted or unsubstituted aryl group, or a substituted or unsubstituted heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings.

13. The display apparatus according to claim 12, wherein said at least one organic electroluminescent device is arranged as a blue-light emitting device(s).

* * * * *